United States Patent [19]

Adams, Jr.

[11] 4,456,469

[45] Jun. 26, 1984

[54] PYRIDYL SULFONE HERBICIDES

[75] Inventor: John B. Adams, Jr., Hockessin, Del.

[73] Assignee: E. I. Du Pont de Nemours and Company, Wilmington, Del.

[21] Appl. No.: 408,491

[22] Filed: Aug. 16, 1982

Related U.S. Application Data

[63] Continuation-in-part of Ser. No. 128,176, Apr. 24, 1980, abandoned.

[51] Int. Cl.$^3$ .................. C07D 251/46; C07D 251/52; A01N 43/70; A01N 43/40

[52] U.S. Cl. ........................................ 71/93; 544/207; 544/209; 544/212

[58] Field of Search ....................... 544/212, 209, 207; 71/93

[56] References Cited

U.S. PATENT DOCUMENTS 4,301,286 11/1981 Schwing et al. .................... 544/211

FOREIGN PATENT DOCUMENTS 1114819 12/1981 Canada ................................ 544/212

13480 7/1980 European Pat. Off. .

*Primary Examiner*—John M. Ford

[57] ABSTRACT

Pyridyl sulfones, e.g., N-[(4,6-dimethylpyrimidin-2-yl)aminocarbonyl]-2-(methylsulfonyl)-3-pyridinesulfonamide, are useful for the regulation of plant growth and as pre-emergence and post-emergence herbicides.

23 Claims, No Drawings

PYRIDYL SULFONE HERBICIDES

RELATED APPLICATION

This application is a continuation-in-part of my copending application U.S. Ser. No. 128,176, filed Apr. 24, 1980, now abandoned.

BACKGROUND OF THE INVENTION

This invention relates to pyridyl sulfones which are useful as agricultural chemicals.

French Pat. No. 1,468,747 discloses the following para-substituted phenylsulfonamides, useful as antidiabetic agents:

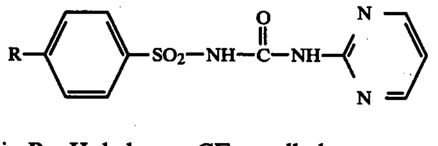

wherein R=H, halogen, $CF_3$ or alkyl.

Logemann et al. Chem. Abstr., 53, 18052g (1959), disclose a number of sulfonamides, including uracil derivatives and those having the formula:

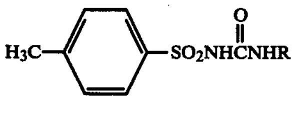

wherein R is butyl, phenyl or

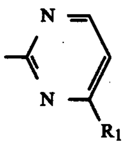

and $R_1$ is hydrogen or methyl. When tested for hypoglycemic effect in rats (oral doses of 25 mg/100 g, the compounds in which R is butyl and phenyl were most potent.

Wojciechowski, Acta Polon. Pharm. 19, p. 121-5 (1962) [Chem. Abstr., 59 1633e] describes the synthesis of N-[(2,6-dimethoxypyrimidin-4-yl)-aminocarbonyl]-4-methylbenzenesulfonamide:

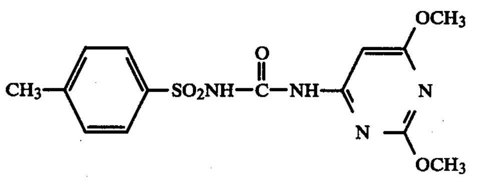

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

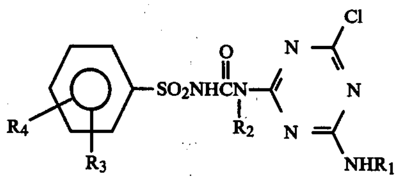 (i)

wherein $R_1$ and $R_2$ may independently be alkyl of 1–4 carbon atoms; and $R_3$ and $R_4$ may independently be hydrogen, chlorine or alkyl of 1–4 carbon atoms.

Compounds of Formula (ii), and their use as antidiabetic agents, are reported in *J. Drug. Res.* 6, 123 (1974).

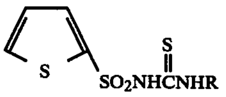 (ii)

wherein R is pyridyl.

In U.S. Ser. No. 029,821, herbicidal compounds such as N-heterocyclic-N'(arylsulfonyl)carbamimidothioates (or compounds wherein a thienyl radical is substituted for the aryl radical), such as methyl N'-(2-chlorophenylsulfonyl)-N-(4-methoxy-6-methylpyrimidin-2-yl)carbamimidothioate are taught.

U.S. Pat. No. 3,689,549 to R. P. Williams discloses "heterocyclic sulfonamides wherein the heteroatoms are inert can be used, e.g., compounds having the furan, thiophene or pyridine nucleus," in the production of sulfonyl isocyanates from sulfonamides in a sulfolane solvent.

B. G. Boggiano, V. Petrow, O. Stephenson and A. M. Wild, in *Journal of Pharmacy and Pharmacology* 13, 567–574 (1961) disclose the following compounds which were tested for hypoglycemic activity.

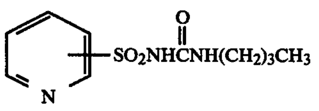

where

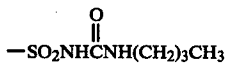

is in the 2 or 3 position.

J. Delarge in *Acta Pol. Pharm.* 34, 245–249 (1977) discloses N-alkylcarbamoylpyridinesulfonamides, as described in the structure below, as mild anti-inflammatory agents and strong diuretics.

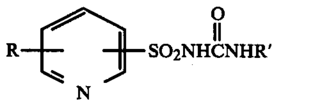

R=3-, 4-, 5-, 6-Me, 2-, 4-, 6-Cl, 3-Br, 4-$Et_2N$, 4-$Me_2CHNH$, 4-(3-$ClC_6H_4$)NH, 4-(3-$CF_3C_6H_4$)NH
R'=Et, Pr, $Me_2CH$, Bu

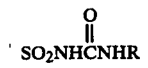

in 2-, 3- and 4-position.

German Pat. No. 2,516,025 Nov. 6, 1975) to J. E. Delarge, C. L. Lapiere and A. H. Georges discloses the following compounds as inflammation inhibitors and diuretics.

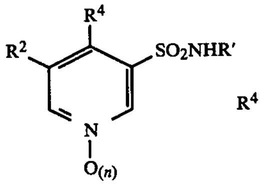

$R^4$ = XR

R=$C_6H_4R^3$ ($R^3$=Cl, $CF_3$, Me, MeO, H, Br, F, $NO_2$, Et, $NH_2$), Et, iso-Pr, 4-methylfuryl, $C_6H_3Cl_2$—, $C_6H_3(CF_3)Cl$;

R'=alkylcarbamoyl, cyclohexylcarbamoyl, arylcarbamoyl, $CSNHCH_2CH{=}CH_2$, $CONHC_6H_4Cl$-p, alkylthiocarbamoyl, H, COEt;

$R^2$=H, Me;

X=NH, NMe, O, S, NEt; and n=0, 1.

U.S. Pat. No. 3,346,590 (Oct. 10, 1967) (to K. Dickere and E. Kühle) discloses the following pyridinesulfonyl isothiocyanates as novel compounds.

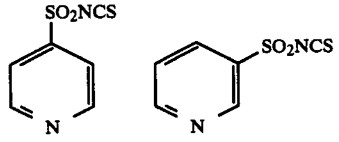

Chem. Abstr. 83 163951p (1975) reports preparation of several 3-substituted 2-alkylsulfonylpyridines:

I

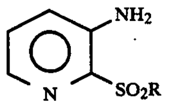

II

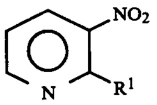

III

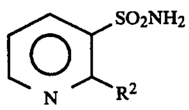

wherein

R=$CH_3$ or $C_2H_5$;

$R^1$=SH, SR, $SO_2R$ or Cl; and $R^2$=Cl, SH or $SO_2C_2H_5$.

Compound II with $R^1$=$SO_2C_2H_5$ is reported to give 96.9% inhibition of gluconeogenesis in rat renal cortex tissue.

The presence of undesired vegetation causes substantial damage to useful crops, especially agricultural products that satisfy man's basic food and fiber needs, such as cotton, rice, corn, wheat, soybean and the like. The current population explosion and concomitant world food and fiber shortage demand improvements in the efficiency of producing these crops. Preventing or minimizing the loss of a portion of such valuable crops by killing or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or control weeds without causing significant damage to useful crops.

SUMMARY OF THE INVENTION

This invention relates to novel compounds of Formula (I), to agricultural compositions containing them, and to their method-of-use as general herbicides having both pre-emergence and post-emergence activity and to their use as plant growth regulants.

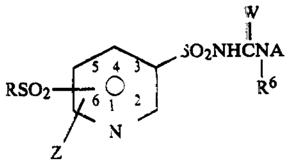

I)

wherein

R is $C_1$–$C_6$ alkyl, $C_3$–$C_6$ alkenyl, $C_2$–$C_4$ alkoxyalkyl, $C_5$–$C_6$ cycloalkyl, $R^1OCH_2CH_2OCH_2$, $R^1OCH_2CH_2OCH_2CH_2$,

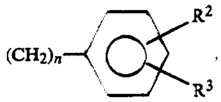

$CF_3$, $CF_3CH_2$ or HGLCCF$_2$, $HCF_2$;

$R^1$ is methyl or ethyl;

$R^2$ and $R^3$ are independently H, Cl, $OCH_3$, F, $CH_3$, Br, $NO_2$ or $CF_3$;

n is 0, 1 or 2;

G is F, Cl, Br or $CF_3$;

L is F, Cl or H;

Z is H, F, Cl, Br, $CH_3$, $CH_3O$ or $CH_3S$;

W is O or S;

A is 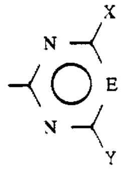 or 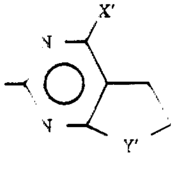

X is $CH_3$, $CH_3O$ or Cl;

Y is $CH_3$, $CH_3CH_2$, $CH_3O$, $CH_3CH_2O$, $CF_3CH_2O$, $CH_3O(CH_2)_m$, $CH_3OCH_2CH_2O$, $R^4O_2CR^5CHO$, $(CH_3)_2N$, $CH_3(CH_2CN)N$, $NHCH_3$ or $NH_2$;

E is CH, N, $CCH_3$, $CCH_2CH_3$ or $CCH_2CH_2Cl$;

$R^4$ is H, $CH_3$ or $CH_3CH_2$;

$R^5$ is H or $CH_3$;

$R^6$ is H or $CH_3$;

m is 1 or 2;

X' is H, $CH_3$, $CH_3O$ or Cl; and

Y' is O or $CH_2$;

and their agriculturally suitable salts provided that:

(1) when W=S, then $R^6$ is H; and (2) when X=Cl, then E=CH and Y=$CH_3$, $C_2H_5$, $CH_3O$, $C_2H_5O$, $CH_3O(CH_2)_m$, $NH_2$, $NHCH_3$ or $N(CH_3)_2$.

Preferred for reasons of their higher herbicidal activity and/or more favorable ease of synthesis are:

(1) Compounds of Formula (I) where

R is $C_1$–$C_6$ alkyl, $C_3$–$C_6$ alkenyl, $C_2$–$C_4$ alkoxyalkyl, $C_5$–$C_6$ cycloalkyl, $R^1OCH_2CH_2OCH_2$, $R^1OCH_2CH_2OCH_2CH_2$,

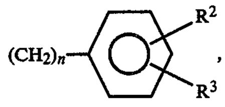

, $CF_3CH_2$ or $HGLCCF_2$;

$R^1$ is methyl or ethyl;

$R^2$ and $R^3$ are independently H, Cl, $OCH_3$, F, $CH_3$, Br, $NO_2$ or $CF_3$;

n is 0, 1 or 2;

G is F, Cl, Br or $CF_3$;

L is F, Cl or H;

Z is H, F, Cl, Br, $CH_3$, $CH_3O$ or $CH_3S$;

W is O or S;

A is 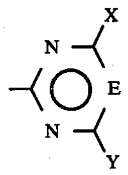 or 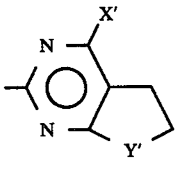 ;

X is $CH_3$ or $CH_3O$;

Y is $CH_3$, $CH_3CH_2$, $CH_3O$, $CH_3CH_2O$, $CF_3CH_2O$, $CH_3O(CH_2)_m$, $CH_3OCH_2CH_2O$, $R^4O_2CR^5CHO$, $(CH_3)_2N$ or $CH_3(CH_2CN)N$;

E is CH, N, $CCH_3$, $CCH_2CH_3$ or $CCH_2CH_2Cl$;

$R^4$ is H, $CH_3$ or $CH_3CH_2$;

$R^5$ is H or $CH_3$;

$R^6$ is H;

m is 1 or 2;

X' is H, $CH_3$, $CH_3O$ or Cl; and

Y' is O or $CH_2$;

and their agriculturally suitable salts.

(2) Compounds of Formula (I) or Preferred 1 wherein the substituent $RSO_2$ is at the 2-position of the pyridine ring.

(3) Compounds of Preferred 2 wherein W is O.

(4) Compounds of Preferred 3 wherein Z is H.

(5) Compounds of Preferred 4 wherein R is $C_1$–$C_4$ alkyl.

(6) Compounds of Preferred 5 where A is

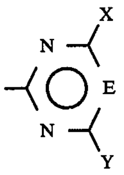

and E is CH or N; and (7) Compounds of Preferred 6 wherein Y is $CH_3$, $CH_3O$ or $CH_3CH_2O$.

Specifically preferred for reasons of their highest herbicidal activity and/or most favorable ease of synthesis are:

N-[(4,6-Dimethylpyrimidin-2-yl)aminocarbonyl]-2-(methylsulfonyl)-3-pyridinesulfonamide, N-[(4-Methoxy-6-methylpyrimidin-2-yl)aminocarbonyl]-2-(methylsulfonyl)-3-pyridinesulfonamide;

N-[(4,6-Dimethoxy-1,3,5-triazin-2-yl)aminocarbonyl]-2-(methylsulfonyl)-3-pyridinesulfonamide;

N-[(4,6-Dimethoxypyrimidin-2-yl)aminocarbonyl]-2-(methylsulfonyl)-3-pyridinesulfonamide;

N-[(4,6-Dimethyl-1,3,5-triazin-2-yl)aminocarbonyl]-2-(methylsulfonyl)-3-pyridinesulfonamide;

N-[(4-Methoxy-6-methyl-1,3,5-triazin-2-yl)aminocarbonyl]-2-(methylsulfonyl)-3-pyridinesulfonamide;

N-[(6,7-Dihydro-4-methyl-5H-cyclopentapyrimidin-2-yl)aminocarbonyl]-2-(methylsulfonyl)-3-pyridinesulfonamide;

N-[(6,7-Dihydro-4-methoxy-5H-cyclopentapyrimidin-2-yl)aminocarbonyl]-2-(methylsulfonyl)-3-pyridinesulfonamide;

N-[(5,6-Dihydro-4-methylfuro[2,3-D]pyrimidin-2-yl)-aminocarbonyl]-2-(methylsulfonyl)-3-pyridinesulfonamide;

N-[(5,6-Dihydro-4-methoxyfuro[2,3-D]pyrimidin-2-yl)-aminocarbonyl]-2-(methylsulfonyl)-3-pyridinesulfonamide;

N-[(4-chloro-6-methoxypyrimidin-2-yl)aminocarbonyl]-2-(methylsulfonyl)-3-pyridinesulfonamide;

and

N-[(4-dimethylamino-6-methoxy-1,3,5-triazin-2-yl)-aminocarbonyl]-2-(methylsulfonyl)-3-pyridinesulfonamide.

DETAILED DESCRIPTION

Synthesis

Pyridinesulfonyl isocyanates IV can be made by the method of Ulrich et al. [J. Org. Chem. 34, 3200 (1969)] from a suitably substituted pyridinesulfonamide (II):

1.

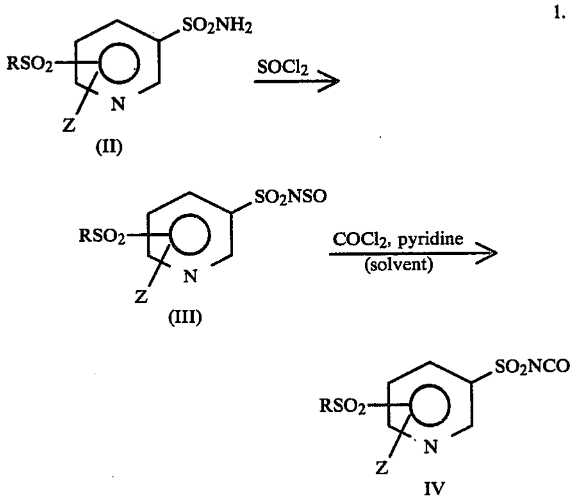

The sulfonamide is boiled under reflux with an excess of thionyl chloride, which functions as a reactant and solvent. The reaction is continued until the sulfonamide protons are undetectable in the proton resonance spectrum. An overnight reaction period (about 16 hours) is frequently sufficient, though several days (e.g. 5) may be required in some cases to convert completely the sulfonamide (II) to the thionylamide (III). Use of a dry-air or oxygen atmosphere during the reflux period can accelerate the rate of reaction of the sulfonamide with the thionyl chloride and improve the yield in cases where conversion in a nitrogen atmosphere is sluggish.

The thionyl chloride is evaporated and the residue treated with an inert solvent (e.g., xylene, toluene, benzene, etc.), at least one equivalent of phosgene, and a catalytic amount of pyridine. The mixture is heated to about 60°-140°, with 80°-100° preferred. Conversion to the isocyanate is substantially complete within about ¼ to 3 hours. The mixture containing the isocyanate can be used directly for the next reaction step [formation of compound (I), with W=O] or isolated and purified by filtration and/or evaporation of solvent.

Compounds of Formula (I) are conveniently prepared by reacting the appropriately substituted pyridinesulfonamide with the appropriate methyl pyrimidinylcarbamate or methyl triazinylcarbamate in the presence of an equimolar amount of trimethylaluminum according to the procedure of reaction 2.

2.

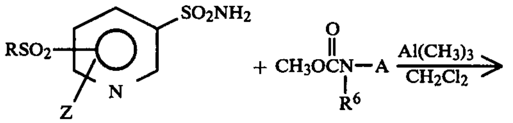

(II)

Ia [Compound (I) with W = O]

Reaction 2 is best carried out in methylene chloride at 25° to 40° for 24 to 96 hours under a nitrogen atmosphere. The product is isolated by addition of an aqueous acetic acid solution followed by extraction of the product into methylene chloride or direct filtration of a product of low solubility. The product is purified by trituration with solvents such as n-butyl chloride or ether or subjected to column chromatography.

Pyridinesulfonyl isothiocyanates VI can be made by the method of Hartke [Chem. Abstr. 64, 15783e (1966)] or U.S. Pat. No. 3,346,590 (see above):

3.

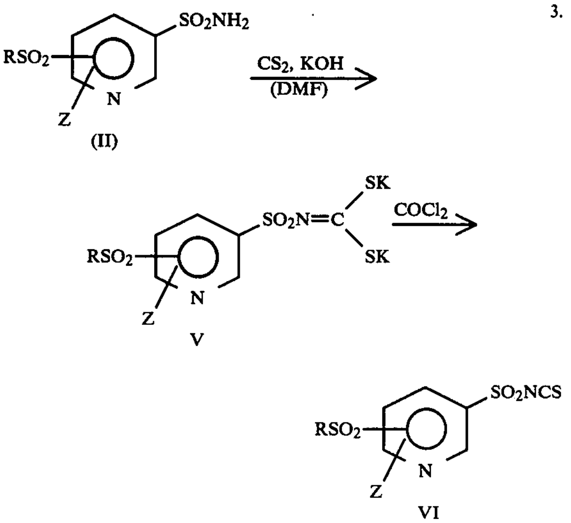

(II) V VI

The sulfonamide in DMF is treated with an equivalent of carbon disulfide and two equivalents of powdered potassium hydroxide at about 35°; other bases, including non-nucleophilic bases such as sodium hydride, can be used instead of KOH. The mixture is stirred (about 1-8 hours) until solution is substantially complete, then diluted with an aprotic solvent (e.g., ethyl acetate) to precipitate the intermediate potassium salt V. The latter is separated by filtration of the reaction mixture, suspended in an inert solvent (e.g., toluene or xylene) and treated with two moles of phosgene (or thionyl chloride, etc.) at about 0°. The mixture is allowed to warm to ambient temperature, filtered and the sulfonyl isothiocyanate used as-is for formation of compound (I), with W=S, or isolated by evaporation of the solvent. The sulfonyl isothiocyanates may dimerize or trimerize in some cases, but the dimers and trimers still produce the compound (I).

The sulfonyl isocyanate IV or isothiocyanate VI reacts with the aminoheterocyclic compound to provide the pyridyl sulfone (I):

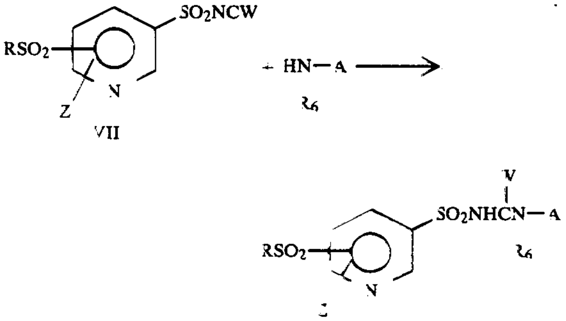

VII (I)

This reaction is best done in an inert organic solvent (such as acetonitrile, tetrahydrofuran, methylene chloride, etc.). The reactants may be added in any order; the reaction is generally exothermic. Conveniently, the starting reaction temperature is ambient, but it can be varied from about 0° to 100° if desired. The product can be isolated by filtration if it precipitates from the reaction mixture; otherwise the solvent can be evaporated and the residual product obtained thereby, with optional purification through trituration with an organic solvent (e.g. diethyl ether, 1-chlorobutane, etc.) in which it is only sparingly soluble, or by recrystallization.

An alternative method for preparation of compounds (I), with W=S, is to react sulfonamide II with a heterocyclic isothiocyanate:

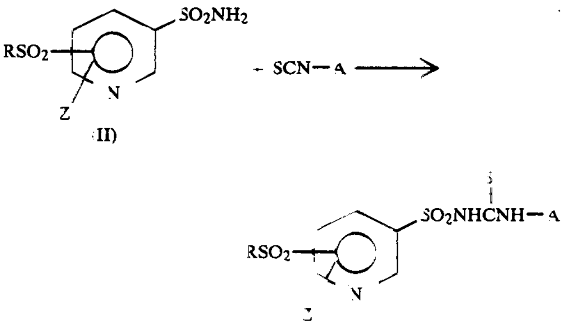

(II)

(I), with W = S

The heterocyclic isothiocyanates used in this procedure can be made, for example, by the method of Japan Patent Application Pub: Kokai No. 51-143686, June 5, 1976, or that of W. Abraham and G. Barnikow Tetrahedron 29, 691 (1973). Reaction 5 is best carried out in an inert, polar solvent (e.g., acetone or butanone) at 20° to 50°, in the presence of a basic catalyst (e.g., $K_2CO_3$ or $Na_2CO_3$), during about 1 to 10 hours. The alkali metal salt of (I), with W=S, is filtered off, suspended in water, and the pH adjusted down to 1-3 with acid (e.g., HCl or $H_2SO_4$) to form pyridyl sulfone (I), with W=S, recovered by filtration.

The starting pyridinesulfonamides (II) can be made by one or more of the illustrative methods shown below:

6.

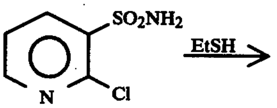

VIII

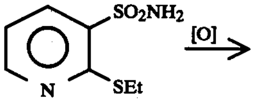

IX

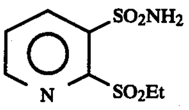

[Ref: Chem. Abstr. 83, 163951p (1975)]

X [compound (II) with R = Et Z = H]

Thus, a mercaptan reacts with the chloropyridine compound in the presence of a base to form the sulfide IX, which is then oxidized to the sulfone X.

7.

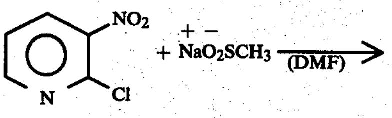

XI

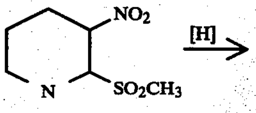

XII

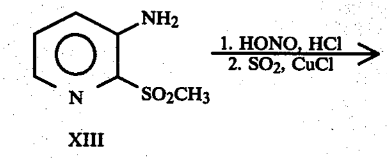

XIII

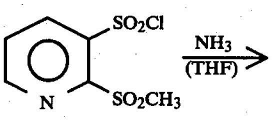

XIV

-continued

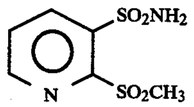

XV

In reaction 7, the chloronitropyridine reacts with sodium methanesulfinate in the presence of a solvent [preferably a polar, aprotic solvent such as N,N-dimethylformamide (DMF), dimethyl sulfoxide (DMSO), N,N-dimethylacetamide (DMAC), tetramethylenesulfone (sulfolane), etc.] at a temperature from about ambient up to the boiling point of the solvent, to provide the sulfone XII.

Other halonitropyridines can be substituted for XI and other sulfinic acid salts for sodium methanesulfinate, depending on the particular sulfone desired. Reduction of compound XII to the amino compound XIII can be accomplished by conventional routes, such as with iron and aqueous acetic acid, or catalytic hydrogenation. Diazotization of the amine XIII at about −10° to 20° (preferably 0° to 10°) in the presence of HCl and subsequent treatment with $SO_2$ and a copper species (such as cuprous or cupric chloride), at about −10° to 50° (preferably about 0° to 30°) produces the sulfonyl chloride XIV. Reacting the chloride XIV with anhydrous ammonia in a solvent [e.g. tetrahydrofuran (THF), methylene chloride, butyl chloride, toluene, diethyl ether, etc.] or with aqueous ammonia produces the sulfonamide XV; the amination can be conveniently accomplished at about −10° to 50°, with 0 to 30 preferred.

When R is haloethyl or halopropyl, the compounds (II) can be prepared as illustrated in reaction 8 for the tetrafluoroethyl compound XVIII:

8.

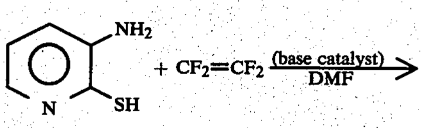

XVI

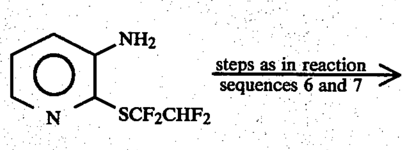

XVII

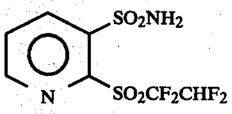

XVIII (compound II with R = $CF_2CHF_2$ Z = H.)

Compound XVI is described in Polish J. Chem. 52, 2041 (1978). Reaction of aminopyridinethiols with the haloalkenes occurs at 0° to 100° in an inert solvent, such as DMF, in the presence of a basic catalyst such as diisopropylamine or potassium hydroxide. The additional steps are carried out as described for reaction sequences 6 and 7.

When R is trifluoromethyl, the compound (II) can be made as shown:

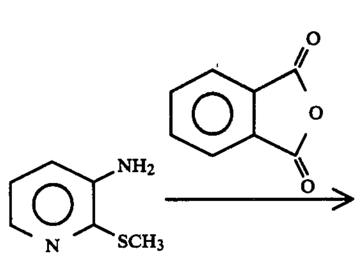

XIX

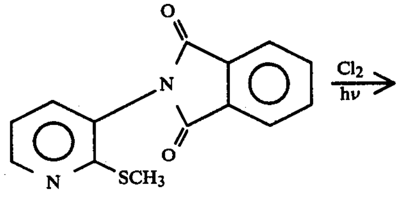

XX

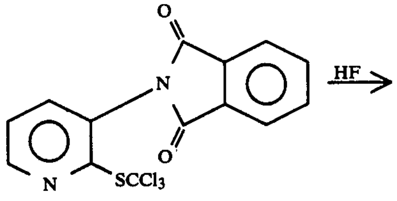

XXI

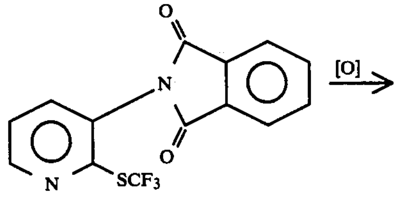

XXII

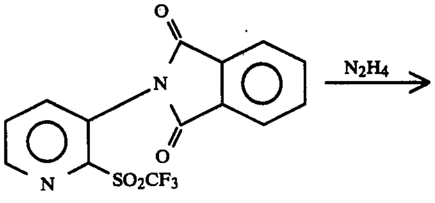

XXIII

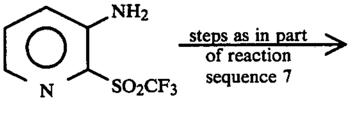

XXIV

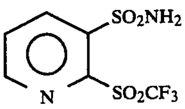

XXV (compound II with R = $CF_3$, Z = H)

[Ref. for similar procedure through compound XXIV: Chem. Abstr. 70, 96324c (1969)].

Thus, the methylthio compound XIX is phthaloylated by phthalic anhydride in acetic acid to compound XX, which is chlorinated photolytically to compound XXI. Halogen exchange is accomplished with HF or $SbF_3$ to prepare compound XXII, which is oxidized to the sulfone XXIII, from which the phthaloyl group is removed by hydrazine to provide the amine XXIV. The amino compound is converted to the sulfonamide as described in reaction sequence 7. Alternatively, the compound XXV with R as trifluoromethyl can be made as shown:

9.

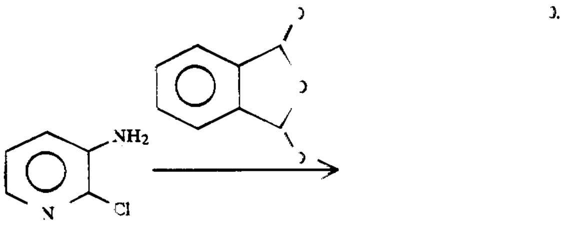

XIX

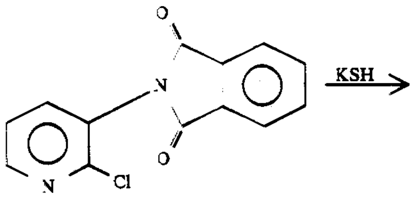

XXVI

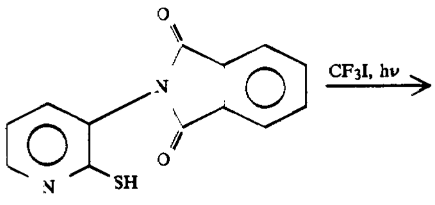

XXVII

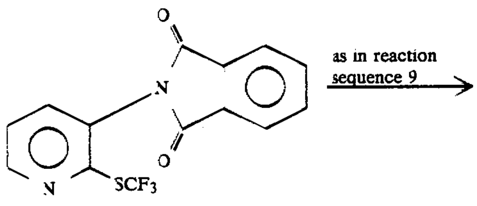

XXII

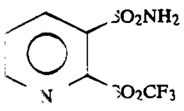

XXV

The chloroaminopyridine is phthaloylated as described for compound XIX. The thiol XXVII is made as mentioned for compound XVI, and the trifluoromethylation is done as described in Chem. Abstr. 87, 134226h, with trifluoroiodomethane.

The synthesis of sulfur compounds of pyridine has been reviewed in "The Chemistry of Heterocyclic Compounds", a series published by Interscience Publ., New York and London. Pyridinesulfonamides are described by H. L. Tale in "Pyridine and Its Derivatives" Supplement, Part 4 (1975), which is incorporated herein by reference.

The compounds of this invention can be made by the teachings discussed, included by reference, or illustrated in the examples and tables which follow, wherein all parts and percentages are by weight and temperatures are in degrees centigrade.

EXAMPLE 1

Preparation of 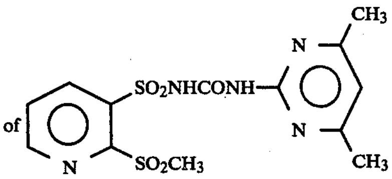

a.

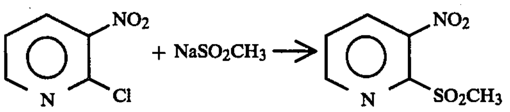

XI XII

A mixture of 22.1 g (0.139 mole) of 2-chloro-3-nitropyridine, 14.5 g (0.142 mole) of sodium methanesulfinate and 150 ml of DMF was boiled under reflux for 1 hour. The DMF was evaporated in vacuum and the residue extracted with ethyl acetate. The ethyl acetate extract was washed with water, dilute brine and saturated brine, dried ($MgSO_4$) and evaporated in vacuum to an oil. The oil was crystallized from butyl chloride and the solid twice recrystallized from acetone/-hexane to provide 9.1 g of the sulfone XII as a tan solid, m.p. 104°-107°.

b.

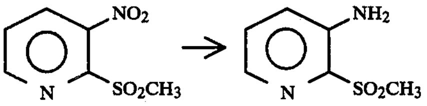

XII XIII

A solution of 9.68 g (0.0479 mole) of the sulfone XII in 50 ml of acetic acid was treated with 12.5 ml of water, then, portionwise with 11.5 g of powdered iron. The temperature was kept at ≦95° during the exothermic reaction by periodic cooling. After an additional 10 minutes at about 83° the mixture was filtered, the filtrate diluted with water and the pH raised to about 6 by gradual addition of 50% NaOH, with cooling to ≦25°; the solution was then evaporated to dryness in vacuum. The residue was treated with ethyl acetate and sodium bicarbonate, the ethyl acetate solution dried ($MgSO_4$), filtered, and evaporated to 7.41 g of a syrup, which was the amine XIII. Mass spectral analysis of the syrup showed the expected molecular ion, m/e 172, for amine XIII.

c.

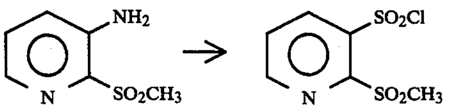

XIII XIV

A solution of 6.73 g (0.0391 mole) of the aminopyridyl sulfone XIII in 9 ml of acetic acid was added to 29 ml of cold conc. HCl at 0° to 10°. The solution was treated, portionwise, at 0° to 5°, with a solution of 3.83 g of sodium nitrite in 10.2 ml of water, with development of an orange color. After an additional 15 minutes at this temperature, the diazonium mixture was added, in portions, to a stirred mixture of 1.1 g of cuprous chloride, 8 ml (liquid) of sulfur dioxide and 42 ml of acetic acid at 5° to 15°; gas evolution occurred rapidly throughout the addition. After an additional 15 minutes, the mixture was warmed to 25°, and the resulting mixture poured into excess ice water. Precipitated white solid was filtered off, washed with water, and dried, providing 5.26 g of the sulfonyl chloride XIV as a white solid, m.p. 162°-163° (dec.).

d.

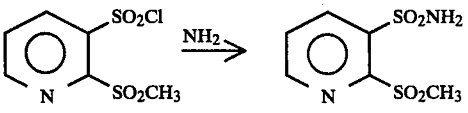

XIV XV

The sulfonyl chloride XIV obtained in Part c was dissolved in THF, cooled in an ice bath and gassed with ammonia, with a resulting exothermic reaction along with the precipitation of a white solid. The mixture was evaporated in vacuum to a white solid, which was washed with water to remove ammonium chloride, leaving the sulfonamide XV as a white solid, m.p. 195°-196.5°. Mass spectral analysis of the solid showed a molecular ion m/e 237 (m+1).

e.

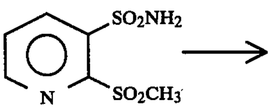

XV

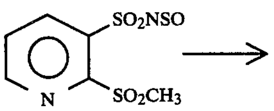

XXVIII

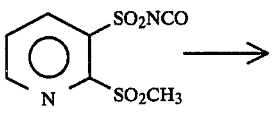

XXIX

-continued

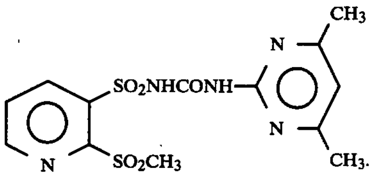

XXX

One gram (0.00423 mole) of the sulfonamide XV was suspended in 100 ml of thionyl chloride. The mixture was boiled under reflux for about 3 days, dissolution of the sulfonamide occurring in 10–15 minutes. The solution was evaporated to a clear, brown oil (XXVIII). An excess of solution of phosgene in toluene (13.8% phosgene solution) was added along with 3–4 drops of pyridine. The mixture was heated at 85° under phosgene reflux for 2 hours, cooled, and filtered. The filtrate was evaporated to a solid (XXIX), which showed a strong isocyanate absorption peak in the infrared spectrum (ca. 2250 $cm^{-1}$, nujol mull).

The solid isocyanate was dissolved in a little acetonitrile and treated with 0.5 g of 2-amino-4,6-dimethylpyrimidine, a reaction quickly occurring with precipitation of white solid. After a few minutes the mixture was filtered and the white solid washed with acetonitrile and butyl chloride, leaving 0.71 g of the pyridyl sulfone XXX as a white solid, m.p. 234° (dec.). Mass spectral analysis showed m/e 236, 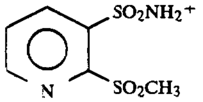 and m/e 149,

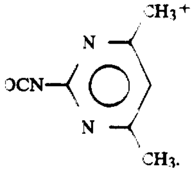

Anal. Calcd. for XXX, $C_{13}H_{15}N_5O_5S_2$(M.W. 385.42): C, 40.5; H, 3.9; N, 18.2. Anal. Found: C, 40.8; H, 4.0; N. 18.5.

TABLE I

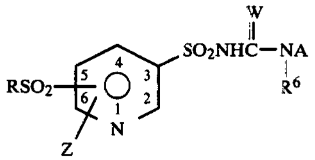

(I)

| $RSO_2$ | Z | W | $R^6$ | A | |
|---|---|---|---|---|---|
| 2-$CH_3SO_2$ | H | O | H | 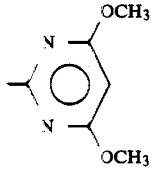 | m.p. 229° dec. |
| 2-$CH_3SO_2$ | H | O | H | 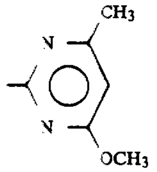 | m.p. 223° dec. |
| 2-$CH_3SO_2$ | H | O | H | 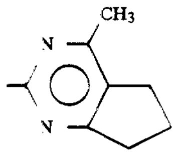 | |
| 2-$CH_3SO_2$ | H | O | H | 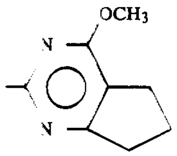 | |
| 2-$CH_3SO_2$ | H | O | H | 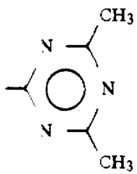 | m.p. 185° dec. |

TABLE I-continued
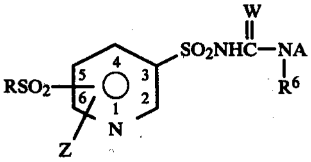
(I)
| RSO2 | Z | W | R6 | A | |
|---|---|---|---|---|---|
| 2-$CH_3SO_2$ | H | O | H | 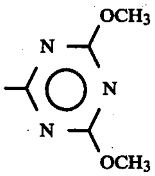 | m.p. 187° dec. |
| 2-$CH_3SO_2$ | H | O | H | 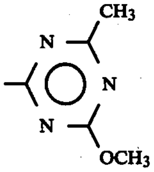 | m.p. 209° dec. |
| 2-$CH_3SO_2$ | H | O | H | 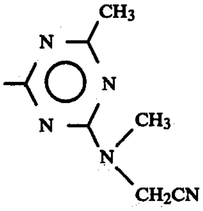 | |
| 2-$CH_3SO_2$ | H | O | H | 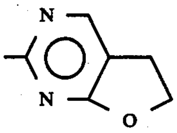 | |
| 2-$CH_3SO_2$ | H | O | H | 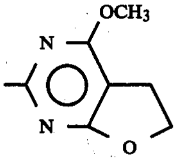 | |
| 2-$CH_3SO_2$ | H | O | H | 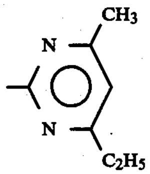 | |
| 2-$CH_3SO_2$ | H | O | H | 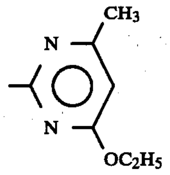 | |
| 2-$CH_3SO_2$ | H | O | H | 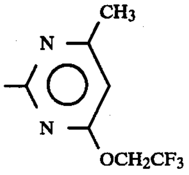 | |

TABLE I-continued
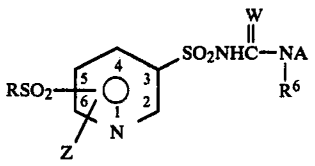
(I)
| RSO2 | Z | W | R6 | A |
| --- | --- | --- | --- | --- |
| 2-$CH_3SO_2$ | H | O | H | 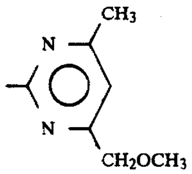 |
| 2-$CH_3SO_2$ | H | O | H | 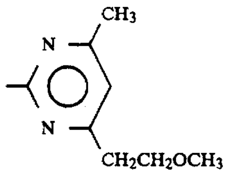 |
| 2-$CH_3SO_2$ | H | O | H | 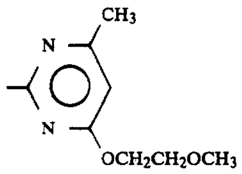 |
| 2-$CH_3SO_2$ | H | O | H | 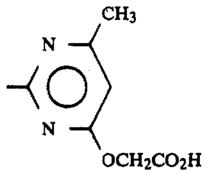 |
| 2-$CH_3SO_2$ | H | O | H | 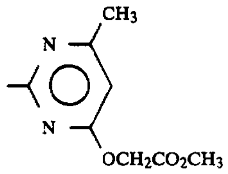 |
| 2-$CH_3SO_2$ | H | O | H | 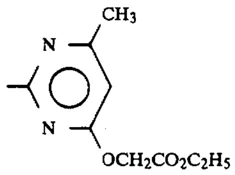 |
| 2-$CH_3SO_2$ | H | O | H | 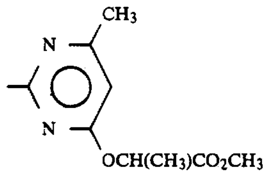 |

TABLE I-continued
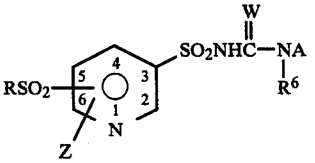
(I)
| RSO2 | Z | W | $R^6$ | A | |
|---|---|---|---|---|---|
| 2-$CH_3SO_2$ | H | O | H | 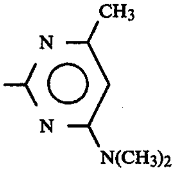 | |
| 2-$CH_3SO_2$ | H | O | H | 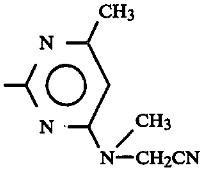 | |
| 2-$CH_3SO_2$ | H | O | H | 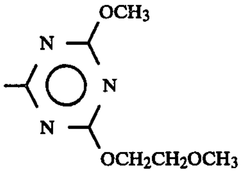 | |
| 2-$CH_3SO_2$ | H | O | H | 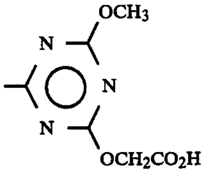 | |
| 2-$CH_3SO_2$ | H | O | H | 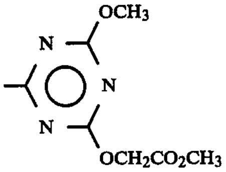 | |
| 2-$CH_3SO_2$ | H | O | H | 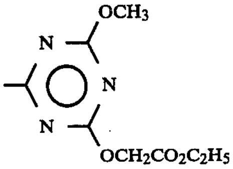 | |
| 2-$CH_3SO_2$ | H | O | H | 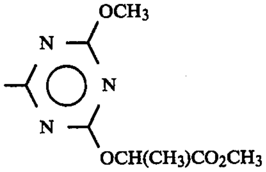 | |
| 2-$CH_3SO_2$ | H | O | H | 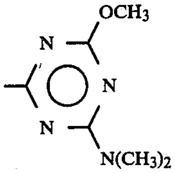 | m.p. 218–220° |

TABLE I-continued
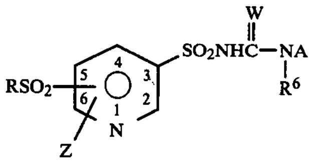 (I)
| RSO2 | Z | W | $R^6$ | A |
|---|---|---|---|---|
| 2-$CH_3SO_2$ | H | O | H | 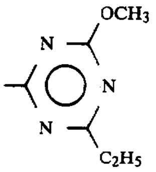 |
| 2-$CH_3SO_2$ | H | O | H | 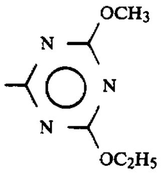 |
| 2-$CH_3SO_2$ | H | O | H | 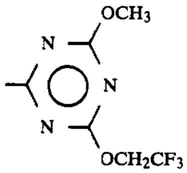 |
| 2-$CH_3SO_2$ | H | O | H | 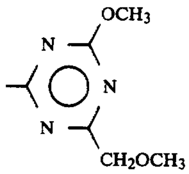 |
| 2-$CH_3SO_2$ | H | O | H | 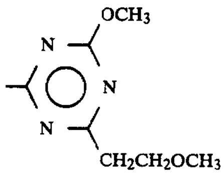 |
| 2-$CH_3SO_2$ | H | O | H | 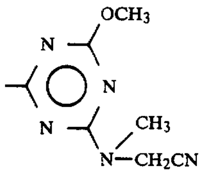 |
| 2-$CH_3SO_2$ | H | O | H | 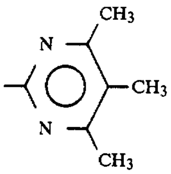 |

TABLE I-continued
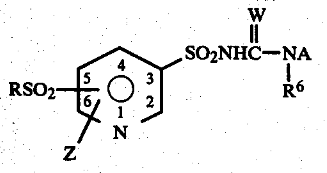
(I)
| RSO2 | Z | W | $R^6$ | A |
|---|---|---|---|---|
| 2-$CH_3SO_2$ | H | O | H | 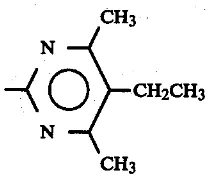 |
| 2-$CH_3SO_2$ | H | O | H | 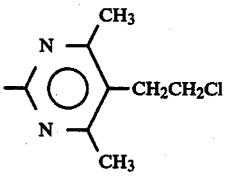 |
| 2-$CH_3SO_2$ | H | O | H | 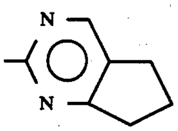 |
| 2-$CH_3SO_2$ | H | O | H | 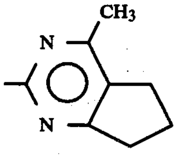 |
| 2-$CH_3SO_2$ | H | O | H | 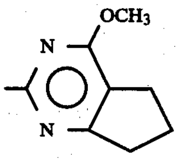 |
| 2-$CH_3SO_2$ | H | O | H | 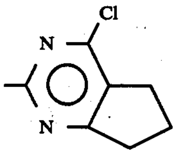 |
| 2-$CH_3SO_2$ | H | O | H | 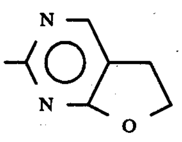 |
| 2-$CH_3SO_2$ | H | O | H | 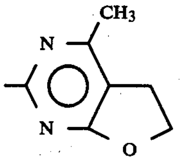 |

TABLE I-continued
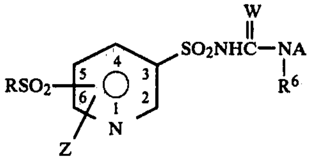
(I)
| $RSO_2$ | Z | W | $R^6$ | A |
| --- | --- | --- | --- | --- |
| 2-$CH_3SO_2$ | H | O | H | 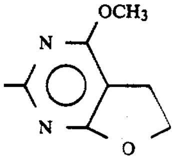 |
| 2-$CH_3SO_2$ | H | O | H | 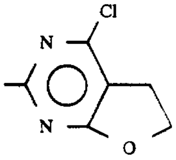 |
| 2-$CH_3SO_2$ | H | O | H | 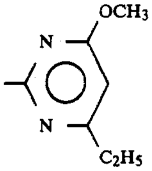 |
| 2-$CH_3SO_2$ | H | O | H | 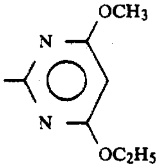 |
| 2-$CH_3SO_2$ | H | O | H | 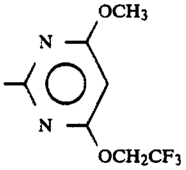 |
| 2-$CH_3SO_2$ | H | O | H | 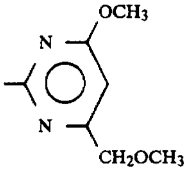 |
| 2-$CH_3SO_2$ | H | O | H | 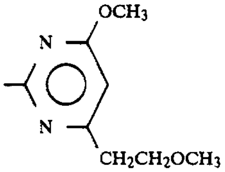 |
| 2-$CH_3SO_2$ | H | O | H | 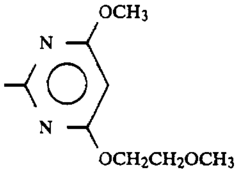 |

TABLE I-continued
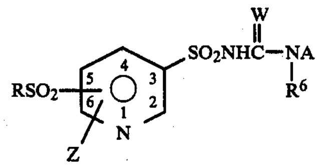
(I)
| $RSO_2$ | Z | W | $R^6$ | A |
|---|---|---|---|---|
| 2-$CH_3SO_2$ | H | O | H | 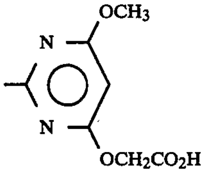 |
| 2-$CH_3SO_2$ | H | O | H | 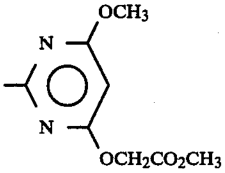 |
| 2-$CH_3SO_2$ | H | O | H | 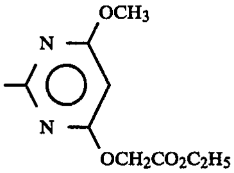 |
| 2-$CH_3SO_2$ | H | O | H | 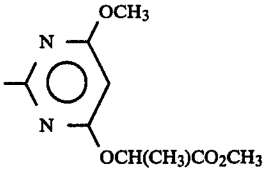 |
| 2-$CH_3SO_2$ | H | O | H | 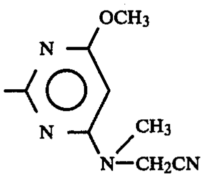 |
| 2-$CH_3SO_2$ | H | O | H | 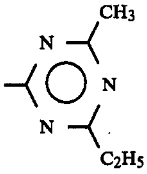 |
| 2-$CH_3SO_2$ | H | O | H | 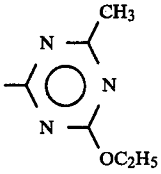 |
| 2-$CH_3SO_2$ | H | O | H | 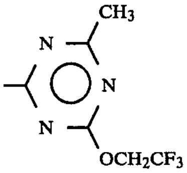 |

TABLE I-continued
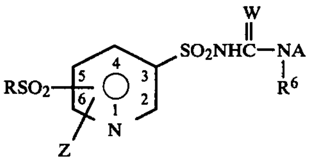
(I)
| RSO2 | Z | W | $R^6$ | A |
|---|---|---|---|---|
| 2-$CH_3SO_2$ | H | O | H | 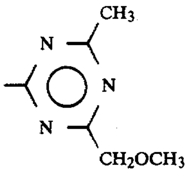 |
| 2-$CH_3SO_2$ | H | O | H | 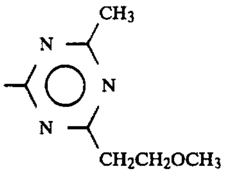 |
| 2-$CH_3SO_2$ | H | O | H | 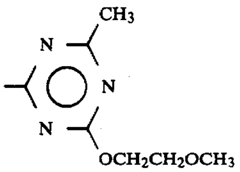 |
| 2-$CH_3SO_2$ | H | O | H | 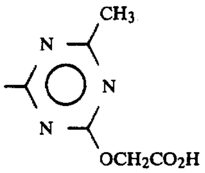 |
| 2-$CH_3SO_2$ | H | O | H | 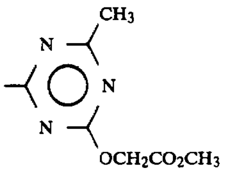 |
| 2-$CH_3SO_2$ | H | O | H | 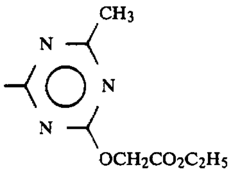 |
| 2-$CH_3SO_2$ | H | O | H | 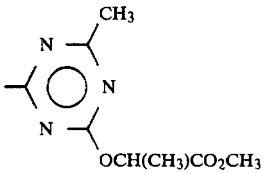 |

TABLE I-continued
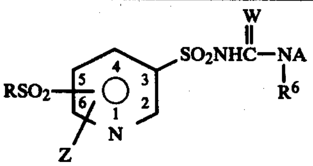
(I)
| $RSO_2$ | Z | W | $R^6$ | A |
|---|---|---|---|---|
| 2-$CH_3SO_2$ | H | O | H | 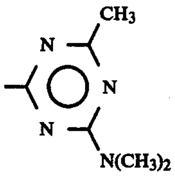 |
| 2-$CH_3SO_2$ | 6-Cl | O | H | 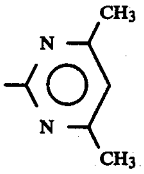 |
| 2-$CH_3SO_2$ | 6-Br | O | H | 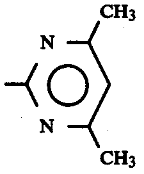 |
| 2-$CH_3SO_2$ | 6-F | O | H | 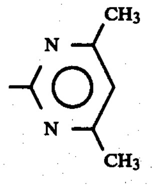 |
| 2-$CH_3SO_2$ | 6-$CH_3$ | O | H | 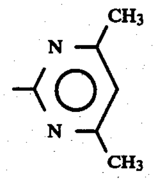 |
| 2-$CH_3SO_2$ | 6-$CH_3O$ | O | H | 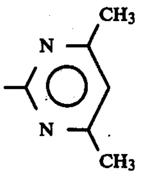 |
| 2-$CH_3SO_2$ | 6-$CH_3S$ | O | H | 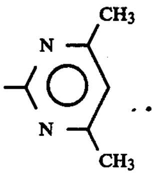 |
| 2-$CH_3SO_2$ | H | S | H | 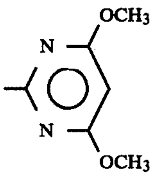 |

TABLE I-continued
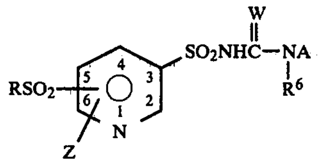
(I)
| RSO2 | Z | W | R6 | A | |
|---|---|---|---|---|---|
| 2-$CH_3SO_2$ | H | S | H | 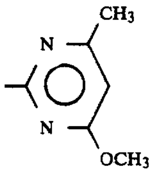 | |
| 2-$CH_3SO_2$ | H | S | H | 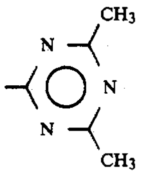 | |
| 2-$CH_3SO_2$ | H | S | H | 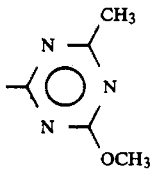 | |
| 2-$CH_3SO_2$ | H | S | H | 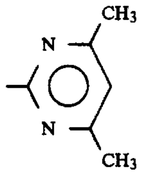 | |
| 2-$CH_3SO_2$ | H | S | H | 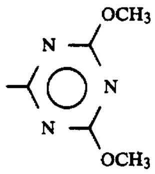 | |
| 2-$CH_3CH_2SO_2$ | H | O | H | 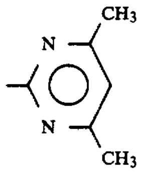 | m.p. 194–196° |
| 2-$CH_3(CH_2)_5SO_2$ | H | O | H | 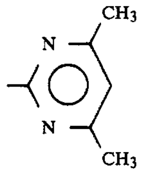 | |

TABLE I-continued
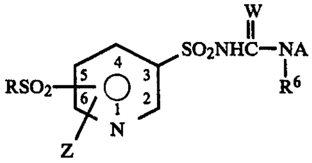
(I)
| $RSO_2$ | Z | W | $R^6$ | A |
|---|---|---|---|---|
| 2-$CH_2$=$CHCH_2SO_2$ | H | O | H | 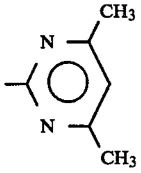 |
| 2-$CH_3(CH_2)_2CH$=$CHCH_2SO_2$ | H | O | H | 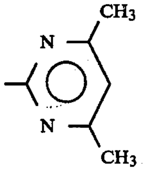 |
| 2-$CH_3OCH_2SO_2$ | H | O | H | 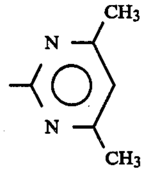 |
| 2-$C_2H_5OCH_2CH_2SO_2$ | H | O | H | 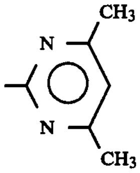 |
| 2-$CH_3OCH_2CH_2OCH_2SO_2$ | H | O | H | 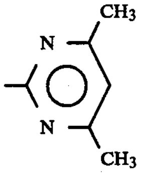 |
| 2-$C_2H_5OCH_2CH_2OCH_2SO_2$ | H | O | H | 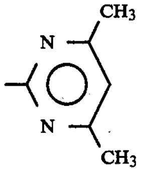 |
| 2-$CH_3OCH_2CH_2OCH_2CH_2SO_2$ | H | O | H | 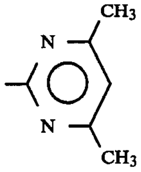 |
| 2-$C_2H_5OCH_2CH_2OCH_2CH_2SO_2$ | H | O | H | 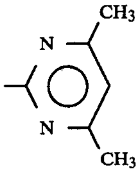 |

TABLE I-continued
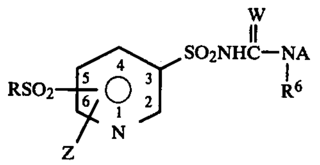
(I)
| RSO2 | Z | W | R6 | A |
|---|---|---|---|---|
| 4-$CH_3SO_2$ | H | O | H | 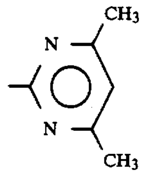 |
| 4-$CH_3SO_2$ | H | O | H | 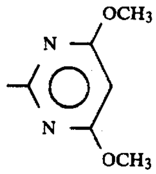 |
| 4-$CH_3SO_2$ | H | O | H | 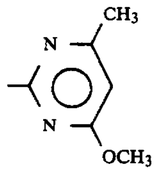 |
| 4-$CH_3SO_2$ | H | O | H | 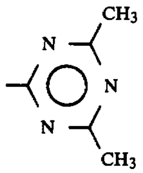 |
| 4-$CH_3SO_2$ | H | O | H | 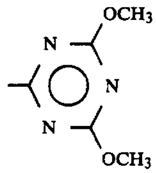 |
| 4-$CH_3SO_2$ | H | O | H | 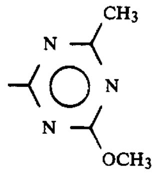 |
| 5-$CH_3SO_2$ | H | O | H | 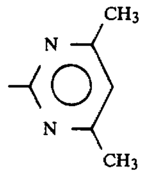 |

TABLE I-continued
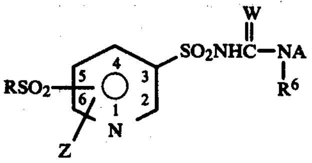
(I)
| $RSO_2$ | Z | W | $R^6$ | A |
|---|---|---|---|---|
| $5-CH_3SO_2$ | H | O | H | 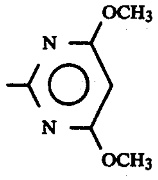 |
| $5-CH_3SO_2$ | H | O | H | 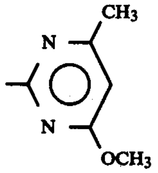 |
| $5-CH_3SO_2$ | H | O | H | 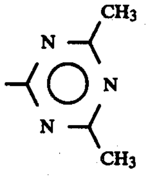 |
| $5-CH_3SO_2$ | H | O | H | 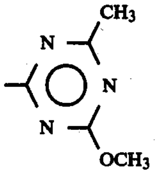 |
| $5-CH_3SO_2$ | H | O | H | 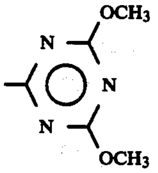 |
| $6-CH_3SO_2$ | H | O | H | 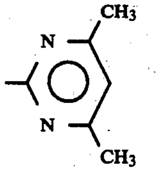 |
| $6-CH_3SO_2$ | H | O | H | 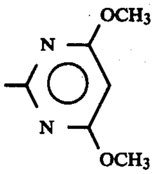 |
| $6-CH_3SO_2$ | H | O | H | 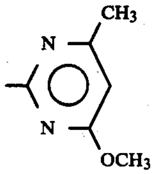 |

TABLE I-continued
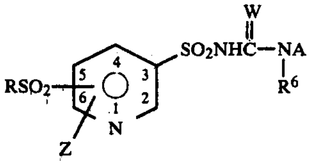
(I)
| $RSO_2$ | Z | W | $R^6$ | A |
|---|---|---|---|---|
| 6-$CH_3SO_2$ | H | O | H | 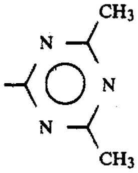 |
| 6-$CH_3SO_2$ | H | O | H | 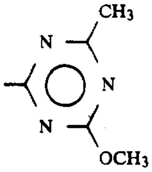 |
| 6-$CH_3SO_2$ | H | O | H | 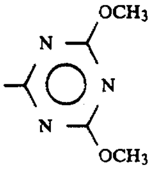 |
| 2-$CH_3SO_2$ | H | O | H | 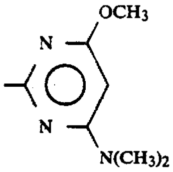 |
| 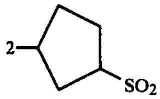 | H | O | H | 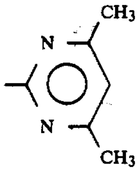 |
| 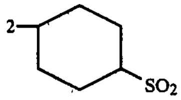 | H | O | H | 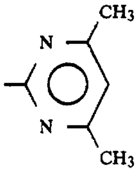 |
| 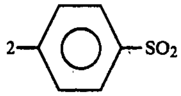 | H | O | H | 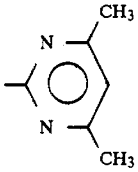 |

TABLE I-continued
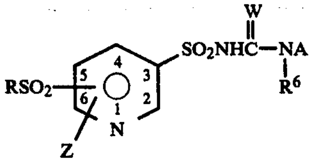
(I)
| $RSO_2$ | Z | W | $R^6$ | A |
|---|---|---|---|---|
| 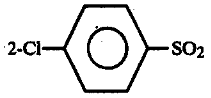 | H | O | H | 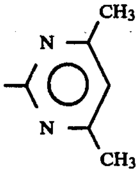 |
| 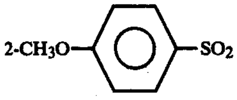 | H | O | H | 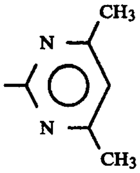 |
| 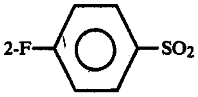 | H | O | H | 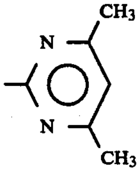 |
| 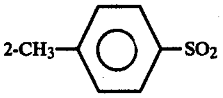 | H | O | H | 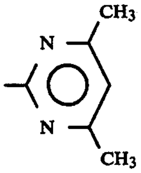 |
| 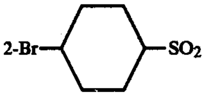 | H | O | H | 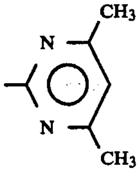 |
| 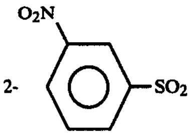 | H | O | H | 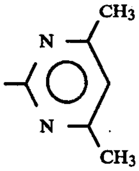 |
| 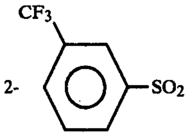 | H | O | H | 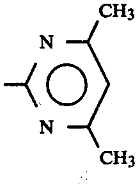 |
| 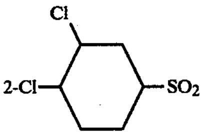 | H | O | H | 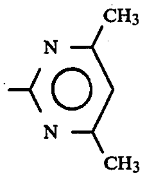 |

TABLE I-continued
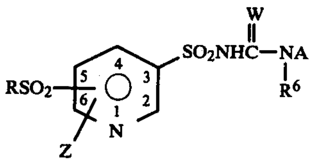 (I)
| $RSO_2$ | Z | W | $R^6$ | A |
|---|---|---|---|---|
| 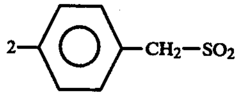 | H | O | H | 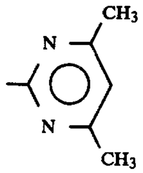 |
| 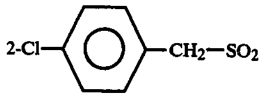 | H | O | H | 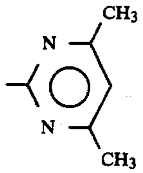 |
| 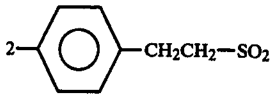 | H | O | H | 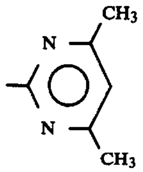 |
| 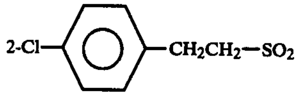 | H | O | H | 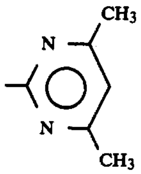 |
| 2-$CF_3SO_2$ | H | O | H | 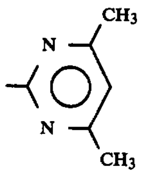 |
| 2-$HCF_2CF_2SO_2$ | H | O | H | 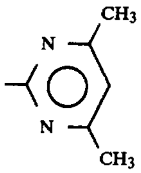 |
| 2-$HCFClCF_2SO_2$ | H | O | H | 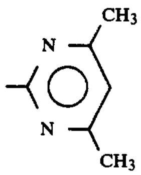 |

TABLE I-continued
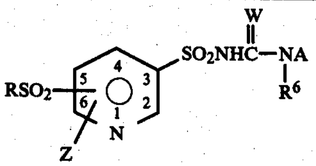
(I)
| $RSO_2$ | Z | W | $R^6$ | A | |
|---|---|---|---|---|---|
| 2-$HCF_2SO_2$ | H | O | H | 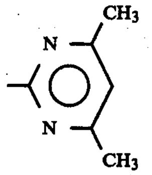 | |
| 2-$HCFBrCF_2SO_2$ | H | O | H | 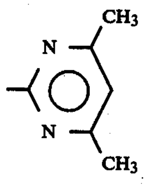 | |
| 2-$CF_3HCFCF_2SO_2$ | H | O | H | 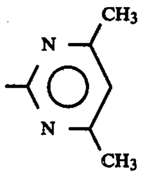 | |
| 2-$HCCl_2CF_2SO_2$ | H | O | H | 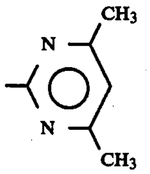 | |
| 2-$H_2CFCF_2SO_2$ | H | O | H | 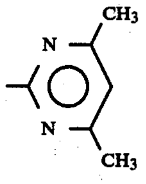 | |
| 2-$CF_3CH_2SO_2$ | H | O | H | 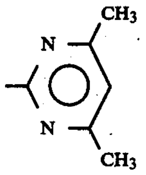 | |
| 2-$CH_3SO_2$ | H | O | H | 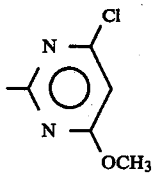 | m.p. 211–212° |
| 2-$CH_3SO_2$ | H | O | H | 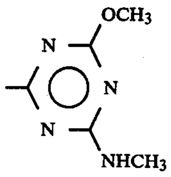 | |

TABLE I-continued
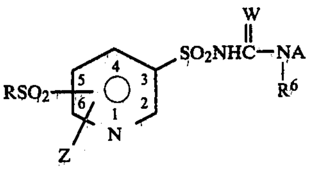
(I)
| RSO2 | Z | W | $R^6$ | A | |
|---|---|---|---|---|---|
| 2-$CH_3SO_2$ | H | O | H | 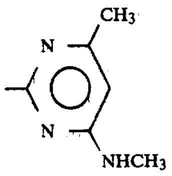 | |
| 2-$CH_3SO_2$ | H | O | $CH_3$ | 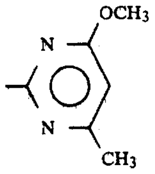 | |
| 2-$CH_3SO_2$ | H | O | $CH_3$ | 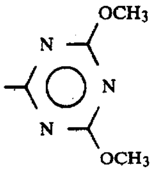 | |
| 2-$CH_3SO_2$ | H | O | $CH_3$ | 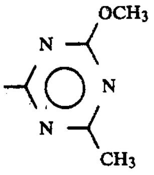 | |
| 2-$CH_3SO_2$ | H | O | $CH_3$ | 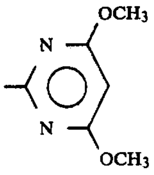 | |
| 2-$CH_3CH_2SO_2$ | H | O | H | 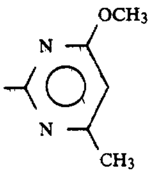 | m.p. 205-209° |
| 2-$CH_3CH_2SO_2$ | H | O | H | 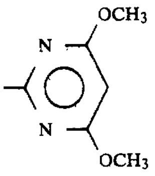 | m.p. 197-200° |

TABLE I-continued
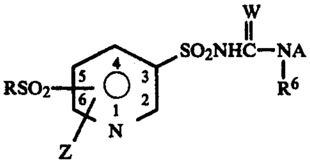
(I)
| $RSO_2$ | Z | W | $R^6$ | A | |
|---|---|---|---|---|---|
| 2-$CH_3CH_2SO_2$ | H | O | H | 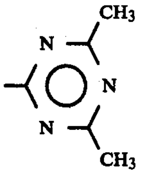 | m.p. 209-211° |
| 2-$CH_3CH_2SO_2$ | H | O | H | 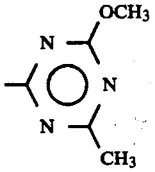 | m.p. 199-201° |
| 2-$CH_3CH_2SO_2$ | H | O | H | 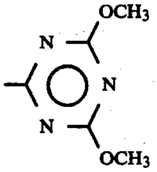 | m.p. 176-179° |
| 2-$(CH_3)_2CHSO_2$ | H | O | H | 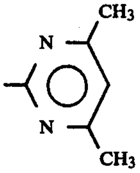 | m.p. 200-202° |
| 2-$(CH_3)_2CHSO_2$ | H | O | H | 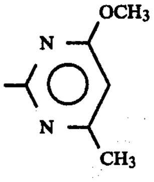 | m.p. 195-198° |
| 2-$(CH_3)_2CHSO_2$ | H | O | H | 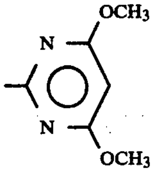 | m.p. 187-192° |
| 2-$(CH_3)_2CHSO_2$ | H | O | H | 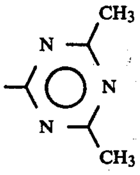 | m.p. 196-198° |
| 2-$(CH_3)_2CHSO_2$ | H | O | H | 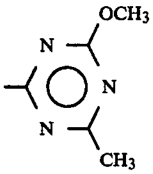 | m.p. 183-185° |

TABLE I-continued
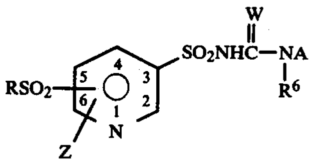
(I)
| $RSO_2$ | Z | W | $R^6$ | A | |
|---|---|---|---|---|---|
| 2-$(CH_3)_2CHSO_2$ | H | O | H | 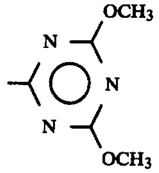 | m.p. 182–184° |
| 2-$CH_3CH_2CH_2SO_2$ | H | O | H | 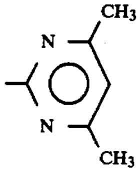 | m.p. 168–172° |
| 2-$CH_3CH_2CH_2SO_2$ | H | O | H | 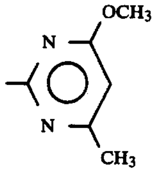 | m.p. 170–174° |
| 2-$CH_3CH_2CH_2SO_2$ | H | O | H | 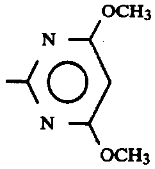 | m.p. 208–211° |
| 2-$CH_3CH_2CH_2SO_2$ | H | O | H | 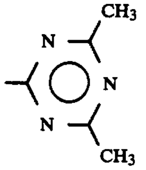 | m.p. 172–174.5° |
| 2-$CH_3CH_2CH_2SO_2$ | H | O | H | 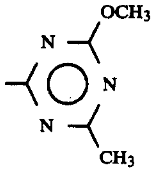 | m.p. 178–183° |
| 2-$CH_3CH_2CH_2SO_2$ | H | O | H | 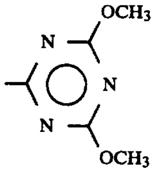 | m.p. 181–185° |

TABLE II

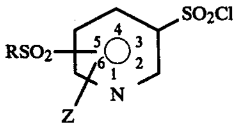

| $RSO_2$ | Z |
|---|---|
| $2\text{-}C_2H_5SO_2$ | H |
| $2\text{-}CH_3(CH_2)_5SO_2$ | H |
| $2\text{-}CH_2{=}CHCH_2SO_2$ | H |
| $2\text{-}CH_3(CH_2)_2CH{=}CHCH_2SO_2$ | H |
| $2\text{-}CH_3OCH_2SO_2$ | H |
| $2\text{-}C_2H_5OCH_2CH_2SO_2$ | H |
| $2\text{-}CH_3OCH_2CH_2OCH_2SO_2$ | H |
| $2\text{-}C_2H_5OCH_2CH_2OCH_2SO_2$ | H |
| $2\text{-}CH_3OCH_2CH_2OCH_2CH_2SO_2$ | H |
| $2\text{-}C_2H_5OCH_2CH_2OCH_2CH_2SO_2$ | H |
| $2\text{-}CH_3SO_2$ | 6-Cl |
| $2\text{-}CH_3SO_2$ | 6-Br |
| $2\text{-}CH_3SO_2$ | 6-F |
| $2\text{-}CH_3SO_2$ | $6\text{-}CH_3$ |
| $2\text{-}CH_3SO_2$ | $6\text{-}CH_3O$ |
| $2\text{-}CH_3SO_2$ | $6\text{-}CH_3S$ |
| $4\text{-}CH_3SO_2$ | H |
| $5\text{-}CH_3SO_2$ | H |
| $6\text{-}CH_3SO_2$ | H |
| 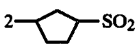 | H |
| 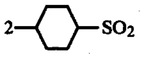 | H |
| 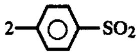 | H |
| 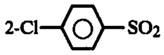 | H |
| 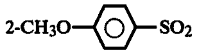 | H |
| 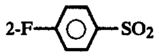 | H |
| 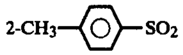 | H |
| 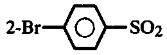 | H |
| 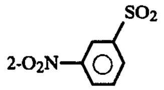 | H |
| 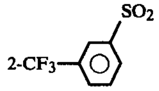 | H |
| 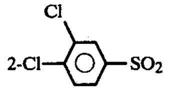 | H |
| 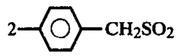 | H |

TABLE II-continued

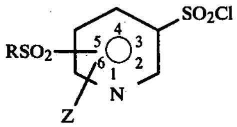

| $RSO_2$ | Z |
|---|---|
| 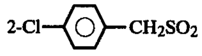 | H |
| 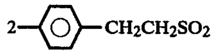 | H |
| 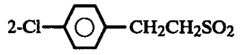 | H |
| $2\text{-}CF_3SO_2$ | H |
| $2\text{-}HCF_2CF_2SO_2$ | H |
| $2\text{-}HCFClCF_2SO_2$ | H |
| $2\text{-}HCFBrCF_2SO_2$ | H |
| $2\text{-}CF_3HCFCF_2SO_2$ | H |
| $2\text{-}HCCl_2CF_2SO_2$ | H |
| $2\text{-}H_2CFCF_2SO_2$ | H |
| $2\text{-}CF_3CH_2SO_2$ | H |
| $2\text{-}HCF_2SO_2$ | H |

TABLE III

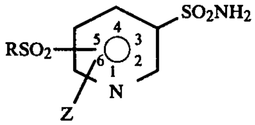

| $RSO_2$ | Z | |
|---|---|---|
| $2\text{-}C_2H_5SO_2$ | H | m.p. 176–177° |
| $2\text{-}CH_3(CH_2)_5SO_2$ | H | |
| $2\text{-}CH_2{=}CHCH_2SO_2$ | H | |
| $2\text{-}CH_3(CH_2)_2CH{=}CHCH_2SO_2$ | H | |
| $2\text{-}CH_3OCH_2SO_2$ | H | |
| $2\text{-}C_2H_5OCH_2CH_2SO_2$ | H | |
| $2\text{-}CH_3OCH_2CH_2OCH_2SO_2$ | H | |
| $2\text{-}C_2H_5OCH_2CH_2OCH_2SO_2$ | H | |
| $2\text{-}CH_3OCH_2CH_2OCH_2CH_2SO_2$ | H | |
| $2\text{-}C_2H_5OCH_2CH_2OCH_2CH_2SO_2$ | H | |
| $2\text{-}CH_3SO_2$ | 6-Cl | |
| $2\text{-}CH_3SO_2$ | 6-Br | |
| $2\text{-}CH_3SO_2$ | 6-F | |
| $2\text{-}CH_3SO_2$ | $6\text{-}CH_3$ | |
| $2\text{-}CH_3SO_2$ | $6\text{-}CH_3O$ | |
| $2\text{-}CH_3SO_2$ | $6\text{-}CH_3S$ | |
| $4\text{-}CH_3SO_2$ | H | |
| $5\text{-}CH_3SO_2$ | H | |
| $6\text{-}CH_3SO_2$ | H | |
| 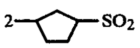 | H | |
| 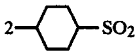 | H | |
| 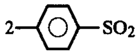 | H | |
| 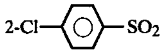 | H | |
| 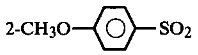 | H | |

TABLE III-continued

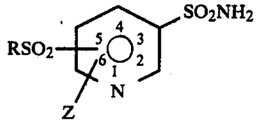

| RSO2 | Z | |
|---|---|---|
| 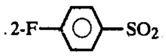 | H | |
| 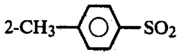 | H | |
| 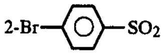 | H | |
| 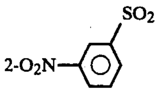 | H | |
| 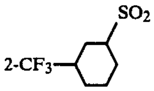 | H | |
| 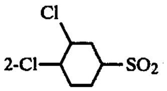 | H | |
| 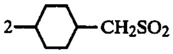 | H | |
| 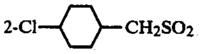 | H | |
| 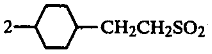 | H | |
| 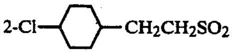 | H | |
| 2-$CF_3SO_2$ | H | |
| 2-$HCF_2CF_2SO_2$ | H | |
| 2-$HCFClCF_2SO_2$ | H | |
| 2-$HCFBrCF_2SO_2$ | H | |
| 2-$CF_3HCFCF_2SO_2$ | H | |
| 2-$HCCl_2CF_2SO_2$ | H | |
| 2-$H_2CFCF_2SO_2$ | H | |
| 2-$CF_3CH_2SO_2$ | H | |
| 2-$CH_3CH_2CH_2SO_2$ | H | m.p. 118–120.5° |
| 2-$(CH_3)_2CHSO_2$ | H | m.p. 132–134° |
| 2-$HCF_2SO_2$ | H | |

TABLE IV

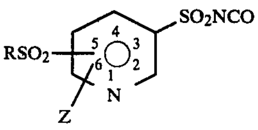

| RSO2 | Z |
|---|---|
| 2-$C_2H_5SO_2$ | H |
| 2-$CH_3(CH_2)_5SO_2$ | H |
| 2-$CH_2{=}CHCH_2SO_2$ | H |
| 2-$CH_3(CH_2)_2CH{=}CHCH_2SO_2$ | H |
| 2-$CH_3OCH_2SO_2$ | H |
| 2-$C_2H_5OCH_2CH_2SO_2$ | H |

TABLE IV-continued

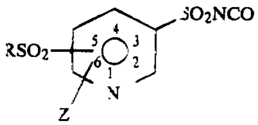

| RSO2 | Z |
|---|---|
| 2-$CH_3OCH_2CH_2OCH_2SO_2$ | H |
| 2-$C_2H_5OCH_2CH_2OCH_2SO_2$ | H |
| 2-$CH_3OCH_2CH_2OCH_2CH_2SO_2$ | H |
| 2-$C_2H_5OCH_2CH_2OCH_2CH_2SO_2$ | H |
| 2-$CH_3SO_2$ | 6-Cl |
| 2-$CH_3SO_2$ | 6-Br |
| 2-$CH_3SO_2$ | 6-F |
| 2-$CH_3SO_2$ | 6-$CH_3$ |
| 2-$CH_3SO_2$ | 6-$CH_3O$ |
| 2-$CH_3SO_2$ | 6-$CH_3S$ |
| 4-$CH_3SO_2$ | H |
| 5-$CH_3SO_2$ | H |
| 6-$CH_3SO_2$ | H |
| 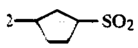 | H |
| 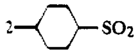 | H |
| 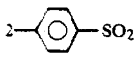 | H |
| 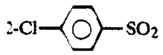 | H |
| 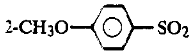 | H |
| 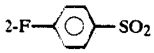 | H |
| 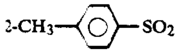 | H |
| 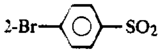 | H |
| 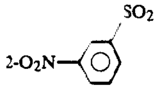 | H |
| 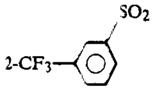 | H |
| 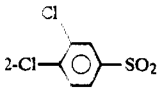 | H |
| 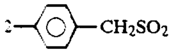 | H |
| 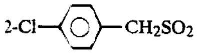 | H |
| 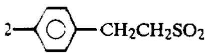 | H |

TABLE IV-continued

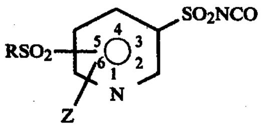

| RSO2 | Z |
|---|---|
| 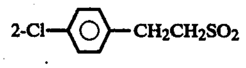 | H |
| 2-$CF_3SO_2$ | H |
| 2-$HCF_2CF_2SO_2$ | H |
| 2-$HCFClCF_2SO_2$ | H |
| 2-$HCFBrCF_2SO_2$ | H |
| 2-$CF_3HCFCF_2SO_2$ | H |
| 2-$HCCl_2CF_2SO_2$ | H |
| 2-$H_2CFCF_2SO_2$ | H |
| 2-$CF_3CH_2SO_2$ | H |
| 2-$HCF_2SO_2$ | H |

TABLE V

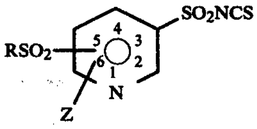

| RSO2 | Z |
|---|---|
| 2-$CH_3SO_2$ | H |
| 2-$C_2H_5SO_2$ | H |
| 2-$CH_3(CH_2)_5SO_2$ | H |
| 2-$CH_2$=$CHCH_2SO_2$ | H |
| 2-$CH_3(CH_2)_2CH$=$CHCH_2SO_2$ | H |
| 2-$CH_3OCH_2SO_2$ | H |
| 2-$C_2H_5OCH_2CH_2SO_2$ | H |
| 2-$CH_3OCH_2CH_2OCH_2SO_2$ | H |
| 2-$C_2H_5OCH_2CH_2OCH_2SO_2$ | H |
| 2-$CH_3OCH_2CH_2OCH_2CH_2SO_2$ | H |
| 2-$C_2H_5OCH_2CH_2OCH_2CH_2SO_2$ | H |
| 2-$CH_3SO_2$ | 6-Cl |
| 2-$CH_3SO_2$ | 6-Br |
| 2-$CH_3SO_2$ | 6-F |
| 2-$CH_3SO_2$ | 6-$CH_3$ |
| 2-$CH_3SO_2$ | 6-$CH_3O$ |
| 2-$CH_3SO_2$ | 6-$CH_3S$ |
| 4-$CH_3SO_2$ | H |
| 5-$CH_3SO_2$ | H |
| 6-$CH_3SO_2$ | H |
| 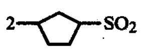 | H |
| 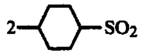 | H |
| 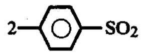 | H |
| 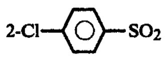 | H |
| 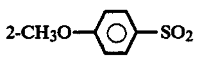 | H |
| 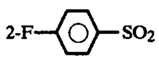 | H |
| 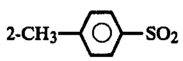 | H |

TABLE V-continued

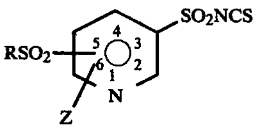

| RSO2 | Z |
|---|---|
| 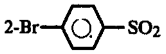 | H |
| 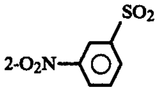 | H |
| 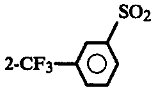 | H |
| 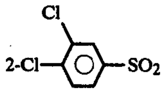 | H |
| 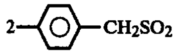 | H |
| 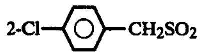 | H |
| 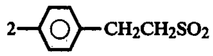 | H |
| 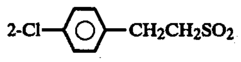 | H |
| 2-$CF_3SO_2$ | H |
| 2-$HCF_2CF_2SO_2$ | H |
| 2-$HCFClCF_2SO_2$ | H |
| 2-$HCFBrCF_2SO_2$ | H |
| 2-$CF_3HCFCF_2SO_2$ | H |
| 2-$HCCl_2CF_2SO_2$ | H |
| 2-$H_2CFCF_2SO_2$ | H |
| 2-$CF_3CH_2SO_2$ | H |
| 2-$HCF_2SO_2$ | H |

Formulations

Useful formulations of the compounds of Formula (I) can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table VI.

TABLE VI

| | Active | Weight Percent* | |
|---|---|---|---|
| | Ingredient | Diluent(s) | Surfactant(s) |
| Wettable Powders | 20-90 | 0-74 | 1-10 |
| Oil Suspensions, | 3-50 | 40-95 | 0-15 |

TABLE VI-continued

| | Active | Weight Percent* | |
|---|---|---|---|
| | Ingredient | Diluent(s) | Surfactant(s) |
| Solutions, Emulsions (including Emulsifiable Concentrates) | | | |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |

*Active Ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates, solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually, grinding as in a hammer or fluid energy mill. Suspensions are prepared by wet milling (see, for example, Littler, U.S. Pat. No. 3,060,084). Granules and pellets may be made by spraying the active material on preformed granular carriers or by agglomeration techniques. See J. E. Browning, "Agglomeration", Chemical Engineering, Dec. 4, 1967, pp. 147ff. and "Perry's Chemical Engineer's Handbook", 4th Ed., McGraw-Hill, New York, 1963, pp. 8-59ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192 Col. 5, line 43 through Col. 7, line 62 and Examples 8, 12, 15, 39, 41, 52, 53, 58, 132, 138-140, 162-164, 166, 167 and 169-182.

H. Gysin and E. Knusli, U.S. Pat. No. 2,891,855, Col. 3, line 66 through Col. 5., line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

Unless indicated otherwise, all parts are by weight in the following examples.

EXAMPLE 2

| Wettable Powder | |
|---|---|
| N—[(4,6-Dimethylpyrimidin-2-yl)aminocarbonyl]-2-(methylsulfonyl)-3-pyridinesulfonamide | 5% |
| dioctyl sodium sulfosuccinate | .1% |
| sodium ligninsulfonate | % |
| synthetic fine silica | .9% |

The ingredients are blended and ground in a hammer-mill to produce particles almost all of which are below 100 microns in size. That material is sifted through a U.S.S. No. 50 screen and packaged.

EXAMPLE 3

| Wettable Powder | |
|---|---|
| N—[(4,6-Dimethylpyrimidin-2-yl)aminocarbonyl]-2-(methylsulfonyl)-3-pyridinesulfonamide | 0% |
| dioctyl sodium sulfosuccinate | .5% |
| sodium ligninsulfonate | % |
| low-viscosity methyl cellulose | .5% |
| attapulgite | 4% |

The ingredients are thoroughly blended and passed through an air mill to produce an average particle size under 15 microns, reblended, and sifted through a U.S.S. No. 50 sieve (0.3 mm opening) before packaging.

EXAMPLE 4

| Granule | |
|---|---|
| wettable powder of Example 3 | 25% |
| gypsum | 64% |
| potassium sulfate | 11% |

The ingredients are blended in a rotating mixer, and water is sprayed onto that blend so as to effect granulation. When most of the granules have reached 1.0 to 0.42 mm (U.S.S. #18 to 40 sieves) in size, they are removed, dried, and screened. Oversize material is crushed to produce additional material in the desired range. The resulting granules contain 10% of the active ingredient.

EXAMPLE 5

| Wettable Powder | |
|---|---|
| N—[(4,6-Dimethylpyrimidin-2-yl)aminocarbonyl]-2-(methylsulfonyl)-3-pyridinesulfonamide | 5% |
| dodecylphenol polyethylene glycol ether | % |
| sodium ligninsulfonate | % |
| sodium silicoaluminate | % |
| montmorillonite (calcined) | 3% |

The ingredients are thoroughly blended. The liquid surfactant is added by spraying on the solid ingredients in a blender. After grinding in a hammer-mill to produce particles almost all of which are below 100 microns in size, the material is reblended, sifted through a U.S.S. #50 sieve (0.3 mm opening) and packaged.

EXAMPLE 6

| Oil Suspension | |
|---|---|
| N—[(4,6-Dimethylpyrimidin-2-yl)aminocarbonyl]-2-(methylsulfonyl)-3-pyridinesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended further with oils or emulsified in water.

EXAMPLE 7

| Aqueous Suspension | |
|---|---|
| N—[(4,6-Dimethylpyrimidin-2-yl)aminocarbonyl]-2-(methylsulfonyl)-3-pyridinesulfonamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to sizes under 10 microns, and then packaged.

EXAMPLE 8

| Extruded Pellet | |
|---|---|
| N—[(4,6-Dimethylpyrimidin-2-yl)aminocarbonyl]-2-(methylsulfonyl)-3-pyridinesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded in the form of cylinders about 3 mm in diameter which are cut to produce pellets about 3 mm long. The pellets may be used directly, after drying, or dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 9

| Solution | |
|---|---|
| N—[(4,6-Dimethylpyrimidin-2-yl)aminocarbonyl]-2-(methylsulfonyl)-3-pyridinesulfonamide | 5% |
| dimethylformamide | 95% |

The ingredients are combined and stirred to produce a solution, which can be used for low-volume applications.

EXAMPLE 10

| Wettable Powder | |
|---|---|
| N—[(4,6-Dimethylpyrimidin-2-yl)aminocarbonyl]-2-(methylsulfonyl)-3-pyridinesulfonamide | 80% |
| sodium alkylnaphthalenesulfonate | 2% |
| sodium ligninsulfonate | 2% |
| synthetic amorphous silica | 3% |

-continued

| Wettable Powder | |
|---|---|
| kaolinite | 13% |

The ingredients are thoroughly blended after grinding in a hammer mill to produce particles essentially all of which are under 100 microns in size; the material is reblended, sifted through a U.S.S. No. 50 sieve and packaged.

EXAMPLE 11

| | |
|---|---|
| N—[(4,6-Dimethylpyrimidin-2-yl)aminocarbonyl]-2-(methylsulfonyl)-3-pyridinesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

Utility

The compounds of the present invention are superior herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.05 to 10 kg/ha, the lower rates being suggested for use on lighter soils and/or those having a low organic matter content, for situations where only short-term persistence is required, or for use as plant growth modifiers.

The compounds of the invention may be used in combination with any other commercial herbicide, examples of which are those of the triazine, triazole, uracil, urea, amide, diphenyl ether, carbamate and bipyridylium types.

The herbicidal and growth modifying properties of the subject compounds were discovered in a number of greenhouse tests. The test procedures and results follow.

Test Procedure A

Seeds of crabgrass (Digitaria spp.), barnyardgrass (*Echinochloa crusgalli*), wild oats (*Avena fatua*), *Cassia tora,* morningglory (Ipomoea spp.), cocklebur (Xanthium spp.), sorghum, corn, soybean, rice, wheat as well as nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three layers, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

C=chlorosis/necrosis;
D=defoliation;
E=emergence inhibition;
G=growth retardation;
H=formative effects;
S=albinism;
U=unusual pigmentation;
X=axillary stimulation; and
6Y=abscised buds or flowers.

The ratings for the compounds tested by this procedure are presented in Table A.

TABLE A
POST-EMERGENCE
| | Rate (kg/ha) | Bush-bean | Cotton | Sorg-hum | Corn | Soybean | Wheat | Wild Oats | Rice | Barn-yard-grass | Crab-grass | Morn-ing Glory | Cock-lebur | Cassia | Nut-sedge | Sugar-beets |
|---|---|---|---|---|---|---|---|---|---|---|---|---|---|---|---|---|
| 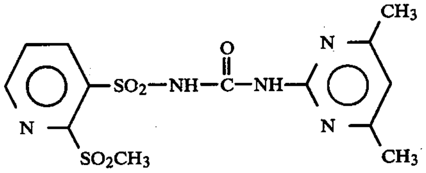<br>Compound 1 | 0.4 | 5C, 9G, 6Y | 9C | 9C | 5U, 9G | 9C | 5C, 8G | 7C | 5C, 7G | 7C, 9H | 9C | 10C | 9C | 5C, 8G | 8G | |
| 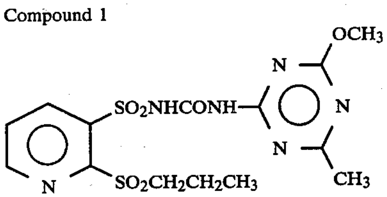<br>Compound 2 | 0.05 | 5C, 9G, 6Y | 4C, 8G | 2C, 8G | 4U, 9C | 4G | 2C, 9G | 2C, 8G | 5C, 9G | 3C, 9H | 2C | 2C, 5H | 3C, 8H | 2C, 5G | 5G | 2C, 8G |
| 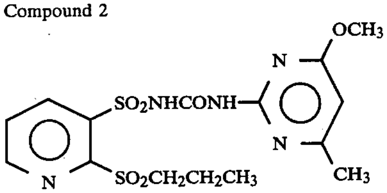<br>Compound 2 | 0.4 | 9C | 10C | 6C, 9G | 6C, 9G | 9C | 6C, 9G | 6C, 9G | 5C, 9G | 9C | 9C | 10C | 10C | 9C | 5C, 9G | 5C, 9G |
| 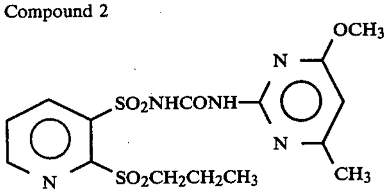<br>Compound 3 | 0.05 | 9C | 6C, 9G | 5C, 9G | 3C, 9G | 4C, 9G | 4C, 9G | 4C, 9G | 4C, 9G | 9C | 3C, 9G | 9C | 10C | 9C | 9G | |
| 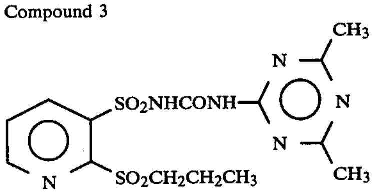 | 0.05 | 5S, 9G, 6Y | — | 2C, 9G | 5C, 9H | 0 | 0 | 2C, 7G | 5C, 9G | 2C, 8H | 2C, 5G | 2C | 1C | 1C | 0 | |

TABLE A-continued
| | | | | | | | | | | | | | | | | |
|---|---|---|---|---|---|---|---|---|---|---|---|---|---|---|---|---|
| Compound 4 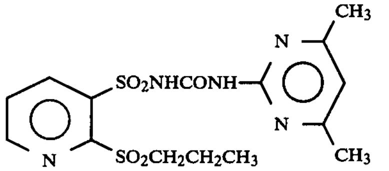 | 0.05 | 9D, 9G, 6Y | 5C, 9G | 9C | 4C, 9G | 2C, 7G | 6C, 9G | 5C, 9G | 5C, 9G | 5C, 9H | 4C, 8G | 5C, 9G | 9C | 9C | 10C | |
| Compound 5 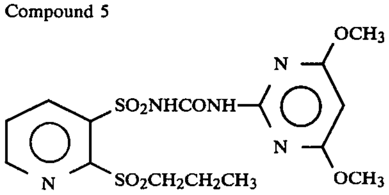 | 0.4 | 9C | 9C | 9C | 9C | 9C | 9C | 9C | 9C | 9C | 9C | 9C | 9C | 9C | 9C | |
| Compound 5 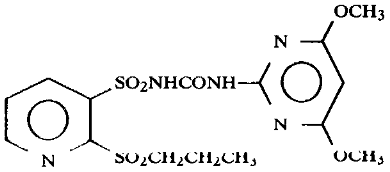 | 0.05 | 9C | 5C, 9G | 9C | 9C | 5C, 9G | 2C, 9H | 2C, 9H | 5C, 9G | 9C | 2C, 8G | 3C, 7G | 9C | 9C | 2C, 8G | |
| Compound 6 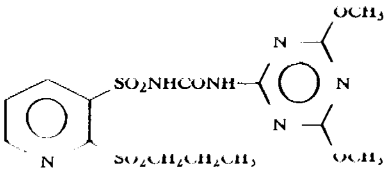 | 0.05 | 9C | | 2C, 9G | 8C, 9G | 2C, 7G | 9C | 2C, 9G | 3C, 9G | 2C, 9H | 2C, 5G | 3C, 7H | 4C, 8H | 3C, 5H | 1C | |
| Compound 7 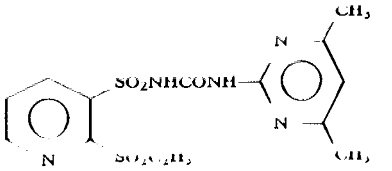 | 0.05 | 9C | 3C, 9G | 9C | 4C, 9G | 2C, 9H | 3C, 9G | 3C, 9G | 3C, 9G | 9C | 3C, 9G | 3C, 9G | 9C | 3C, 9G | 3C, 9G | 3C, 9H |
Compound 8

TABLE A-continued
| | | | | | | | | | | | | | | | | |
|---|---|---|---|---|---|---|---|---|---|---|---|---|---|---|---|---|
| 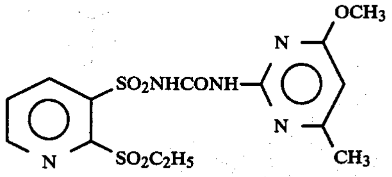 Compound 9 | 0.05 | 5C, 9G, 6Y | 6C, 9G | 9C | 9C | 5C, 9G | 9C | 9C | 5C, 9G | 9C | 5C, 9G | 5C, 9H | 10C | 9C | 2C, 9G | 9C |
| 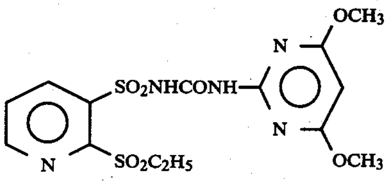 Compound 10 | 0.05 | 9C | 9C | 9C | 10C | 9C | 9C | 9C | 9C | 9C | 9C | 2C, 7G | 10C | 9C | 10C | 9C |
| 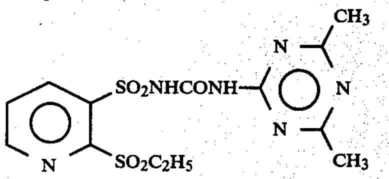 Compound 11 | 0.05 | 3C, 3H, 6Y | 2C | 2U, 9G | 5U, 9G | 1B, 3G | 2C, 9G | 6G | 4C, 9G | 2C, 9H | 3G | 1C, 1H | 4G | 2G | 5G | 2G |
| 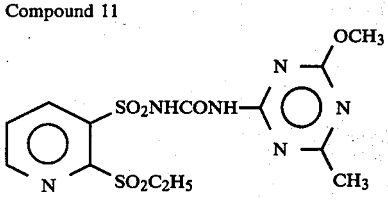 Compound 12 | 0.05 | 6C, 9G, 6Y | 4C, 8G | 3U, 9C | 10C | 3C, 8H | 9C | 2C, 8G | 6C, 9G | 9C | 2C, 9G | 3C, 6G | 2H, 8G | 3C, 7H | 8G | 4C, 9H |
| 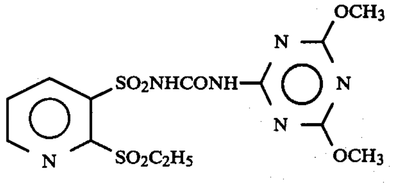 Compound 13 | 0.05 | 5C, 9G, 6Y | 5C, 8G | 4U, 9C | 9C | 3C, 8H | 5C, 9G | 5C, 9G | 5C, 9G | 5C, 9H | 5C, 9H | 2C, 7G | 3C, 9H | 3C, 7H | 6G | 5C, 9G |

TABLE A-continued
| | | | | | | | | | | | | | | | | |
|---|---|---|---|---|---|---|---|---|---|---|---|---|---|---|---|---|
| 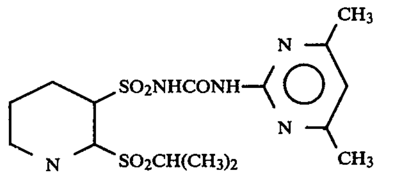 Compound 14 | 0.05 | 5G, 6Y | 4C, 5H | 3C, 9G | 2C, 5H | 1H | 5G | 6G | 9G | 2C, 9H | 3G | 4C, 8G | 3C, 8H | 3C | 2G | 3C, 9H |
| 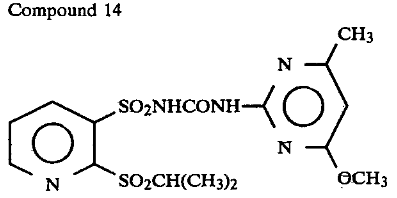 Compound 15 | 0.05 | 3C, 9G, 6Y | 2C, 8G | 3C, 9G | 3U, 9G | 3C, 9G, 5X | 2U, 9G | 3C, 9G | 5C, 9G | 9C | 3C, 9G | 6C, 9G | 9C | 4C, 9G | 3C, 9G | 5C, 9G |
| 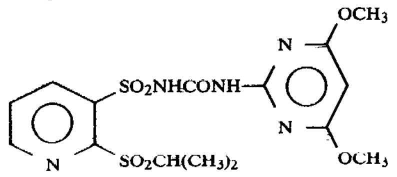 Compound 16 | 0.05 | 9C | 4C, 9G | 9C | 5U, 9G | 4C, 9G | 6C, 9G | 5C, 9G | 5C, 9G | 9C | 5C, 9G | 9C | 10C | 6C, 9G | 5C, 9G | 9C |
| 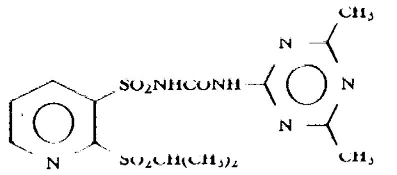 Compound 17 | 0.05 | 1H | 2C | 1C, 4H | 2C, 6H | 2G | 0 | 0 | 8G | 1C, 2H | 0 | 0 | 0 | 0 | 4G | 0 |
| 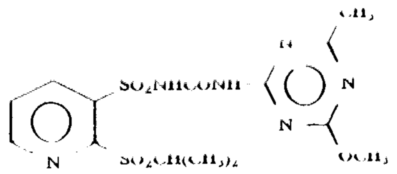 Compound 18 | 0.05 | [illegible] | [illegible] | [illegible] | [illegible] | 4H | [illegible] | [illegible] | [illegible] | [illegible] | [illegible] | [illegible] | [illegible] | [illegible] | [illegible] | [illegible] |

TABLE A-continued
| | | | | | | | | | | | | | | | | |
|---|---|---|---|---|---|---|---|---|---|---|---|---|---|---|---|---|
| 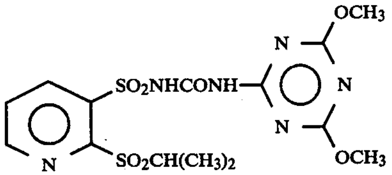<br>Compound 19 | 0.05 | 2C, 3G, 6Y | 2C, 3H | 5C, 9G | 5U, 9C | 3H, 5G, 7X | 5C, 9G | 4C, 9H | 5C, 9G | 5C, 9H | 3C, 8G | 3C, 8G | 3C, 7G | 3C, 5G | 5G | 3C, 5H |
| 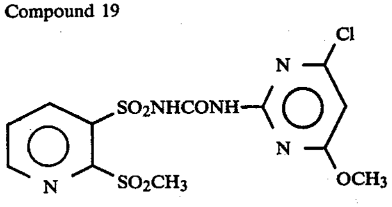<br>Compound 20 | .05 | 3C, 9G, 6Y | 5C, 9G | 9C | 9C | 4H, 8G | 2C, 7G | 8G | 9C | 5C, 9H | 4C, 9H | 8G | 10C | 5C, 9G | 5C, 9G | 9C |
| 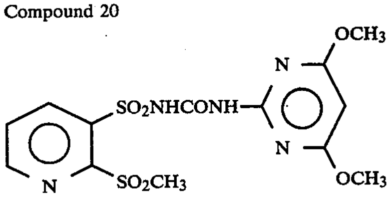<br>Compound 21 | .5 | 9C | 6C, 9G | 10C | 10C | 9C | 9C | 10C | 8C | 9C | 9C | 3C, 9G | 9C | 9C | 9C | — |
| 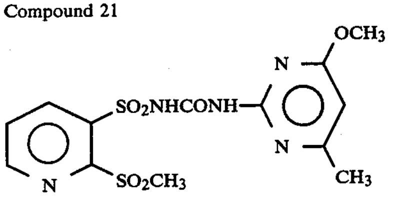<br>Compound 22 | .5 | 9C | 6C, 9G | 9C | 7U, 10C | 9C | 9C | 9C | 6C, 9G | 9C | 9C | 6C, 9G | 9C | 9C | 4C, 5G | — |
| 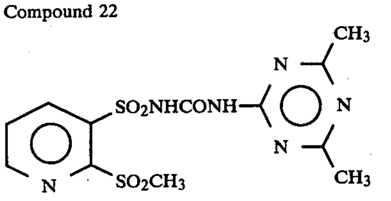<br>Compound 23 | .5 | 2C | 1C | 2C, 8G | 3U, 7G | 2G | 2C, 6G | 1C, 5G | 2C, 6G | 2C, 6H | 4C, 5G | 0 | 0 | 1C | 0 | — |

TABLE A-continued
| | | | | | | | | | | | | | | | | |
|---|---|---|---|---|---|---|---|---|---|---|---|---|---|---|---|---|
| 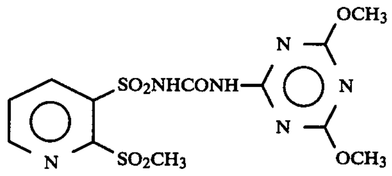 | .5 | 5C, 9G, 6Y | 2C, 3H, 5G | 9C | 8U, 9C | 1C, 2H, 5G | 5U, 9C | 9C | 6C, 9G | 9C | 2C, 8G | 2C, 4G | 1C, 2H | 1C, 4G | 2G | — |
| Compound 24<br>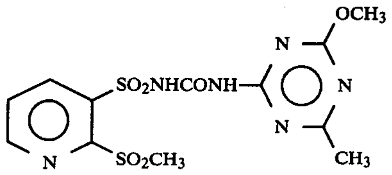 | .5 | 9D, 9G, 6Y | 2C, 2H, 5G | 10C | 8U, 9C | 3C, 8H | 9C | 9C | 9C | 9C | 3C, 7G | 2C, 6G | 2C, 5H | 2C, 3H | 2C, 7G | |
| Compound 25<br>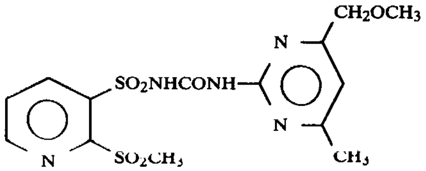 | .05 | 3C, 9G, 6Y | 3C, 3H, 9G | 5C, 9G | 4U, 9G | 2C, 7G, 5X | 2C, 9G | 2C, 9G | 5C, 9G | 9C | 2C, 9H | 0 | 5G | 3C, 3H | 7G | — |
| Compound 26<br>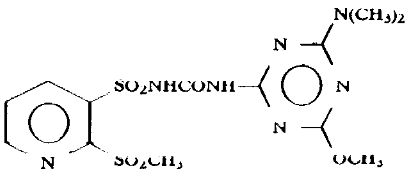 | .05 | 6C, 9G, 6Y | 5C, 9G | 3C, 9G | 9C | 3C, 9G | 9C | 9C | 5C, 9G | 2C, 8H | 2C, 8G | 1C | 4C, 9G | 2C, 5G | 0 | |
PRE-EMERGENCE
| Rate (kg/ha) | Sorghum | Corn | Soybean | Wheat | Wild Oats | Rice | Barnyard grass | Crabgrass | Morning Glory | Cocklebur | Cassia | Nutsedge | Sugarbeets |
|---|---|---|---|---|---|---|---|---|---|---|---|---|---|

TABLE A-continued
| | | | | | | | | | | | | | | |
|---|---|---|---|---|---|---|---|---|---|---|---|---|---|---|
| 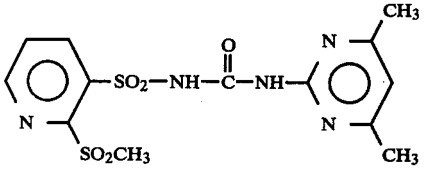 Compound 1 | 0.4 | 5C, 9H | 9H | 9H | 9H | 3C, 8H | 10E | 9H | 2C, 9G | 9G | 9H | 9G | 10E | |
| 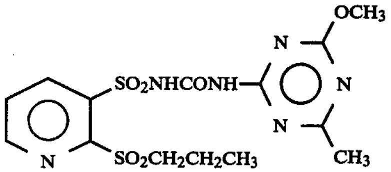 Compound 2 | 0.05 | 4C, 9G | 4C, 9H | 1C | 2C, 9G | 4C, 9H | 9H | 2C | 0 | 5H | 2C, 3H | 1C | 0 | 4C, 6G |
| 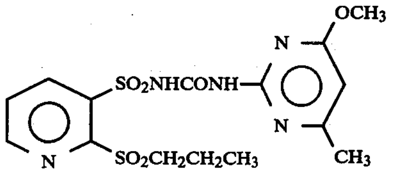 Compound 2 | 0.4 | 5C, 9H | 9H | 9H | 9H | 5C, 9H | 10E | 5C, 9H | 5C, 9G | 9C | 9H | 9G | 10E | |
| 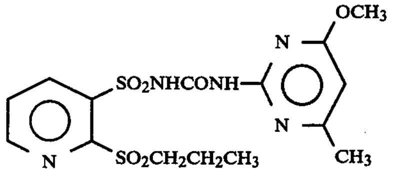 Compound 3 | 0.05 | 5C, 9H | 9G | 9H | 2C, 9H | 3C, 9H | 10E | 2C, 9H | 3C, 8G | 9G | — | 9G | 10E | |
| 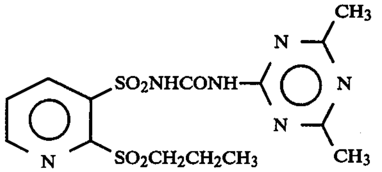 Compound 4 | 0.05 | 3C, 6G | 2C, 5G | 0 | 0 | 0 | 2C, 6H | 0 | 3G | 2G | 0 | 2C | 0 | |

TABLE A-continued
| | | | | | | | | | | | | | | |
|---|---|---|---|---|---|---|---|---|---|---|---|---|---|---|
| 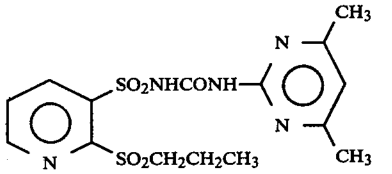 Compound 5 | 0.05 | 8C, 9H | 9H | 2C, 5H | 9H | 3C, 8H | 10E | 9H, 2C | 3C, 8G | 8G | 9H | 8G | 9G | |
| 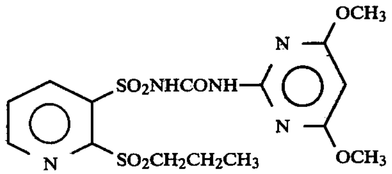 Compound 5 | 0.4 | 10H | 10H | 9H | 9H | 5C, 9H | 10E | 5C, 9H | 10E | 9G | 9H | 10C | 10E | |
| 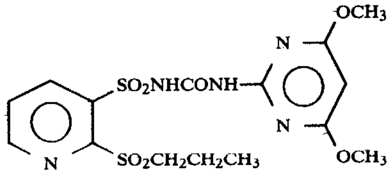 Compound 6 | 0.05 | 2C, 9H | 2C, 9H | 6H | 9H | 2C, 8G | 10E | 2C, 9H | 4C, 9G | 7G | 9H | 9G | 10E | |
| 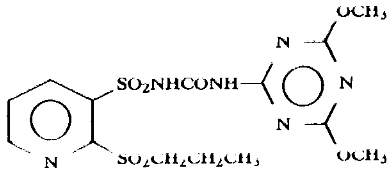 Compound 7 | 0.05 | 5C, 9H | 9H | 1G | 5C, 9H | 2C, 7H | 5C, 9H | 2C, 5G | 2C | 9G | 8H | 2C, 5H | 7G | |
| 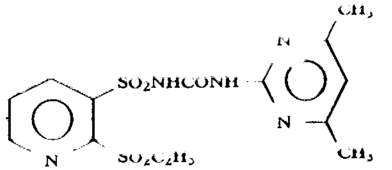 Compound 8 | 0.05 | 10H | 3C, 9H | 3C, 8H | 10H | 8C, 9H | 10E | 3C, 9H | 2C, [illegible] | [illegible] | 9H | 9G | 10E | 10C |

TABLE A-continued
| | | | | | | | | | | | | | | |
|---|---|---|---|---|---|---|---|---|---|---|---|---|---|---|
| 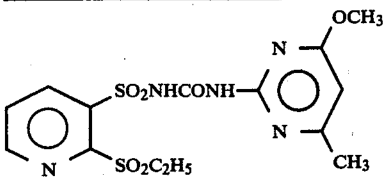 Compound 9 | 0.05 | 10H | 10H | 9H | 9C | 9C | 10E | 6C, 9H | 6C, 9G | 9C | 9H | 9C | 10E | 10E |
| 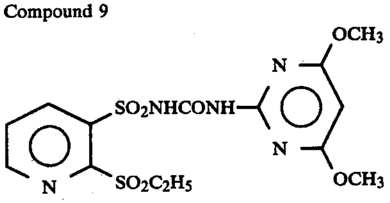 Compound 10 | 0.05 | 10H | 5C, 9H | 9H | 6C, 9H | 6C, 9G | 10E | 5C, 9H | 5C, 9H | 9C | 9H | 9C | 10E | 10E |
| 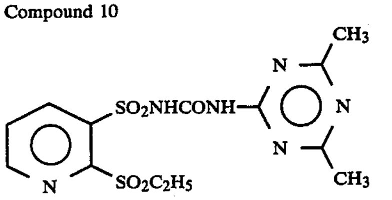 Compound 11 | 0.05 | 2C, 5H | 8G | 0 | 6G | 0 | 8G | 0 | 0 | 2C, 2H | 8H | 0 | 0 | 4G |
| 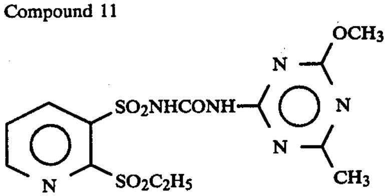 Compound 12 | 0.05 | 5C, 9H | 6C, 9H | 2C, 2H, 5G | 3C, 9G | 3C, 9G | 10E | 3C, 8H | 1C | 9C | 9H | 8G | 5G | 2C, 8G |
| 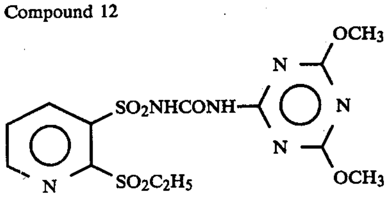 Compound 13 | 0.05 | 6C, 9H | 3C, 9G | 1C, 1H | 3C, 9G | 3C, 9G | 10E | 7H | 0 | 8H | 8H | 8H | 0 | 8G |

TABLE A-continued
| | | | | | | | | | | | | | | |
|---|---|---|---|---|---|---|---|---|---|---|---|---|---|---|
| 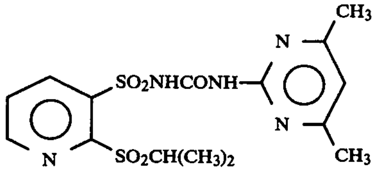 Compound 14 | 0.05 | 3C, 7H | 2C, 6H | 0 | 0 | 2G | 2C, 8G | 2G | 2G | 2C | 7H | 0 | 3G | 8G |
| 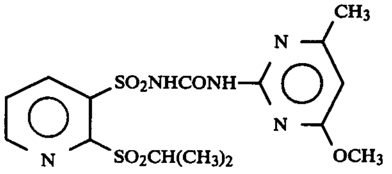 Compound 15 | 0.05 | 7C, 9H | 10H | 8H | 3C, 9H | 5C, 9H | 10E | 3C, 9H | 3C, 7G | 9G | 9H | 3C, 9G | 10E | 10C |
| 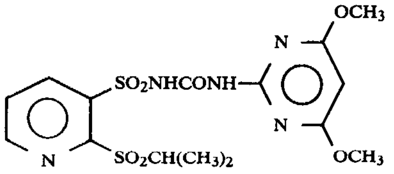 Compound 16 | 0.05 | 9H | 4C, 9G | 8H | 3C, 9G | 4C, 9H | 10E | 5C, 9H | 5C, 8G | 9H | 9H | 9G | 10E | 10E |
| 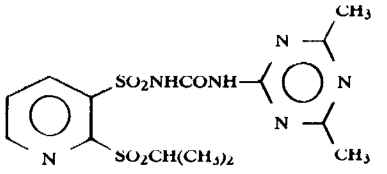 Compound 17 | 0.05 | 0 | 0 | 0 | 0 | 0 | 0 | 0 | 0 | 0 | 0 | 0 | 0 | 0 |
| 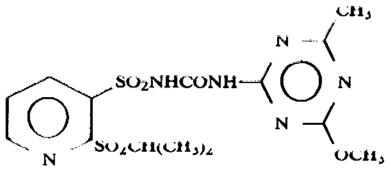 Compound 18 | 0.05 | 3C, 9H | 2C, 9G | 1C | 2C, 8G | 8G | 10E | 8H | 0 | 2C | 8H | 0 | 0 | 1H |

TABLE A-continued
| | | | | | | | | | | | | | | |
|---|---|---|---|---|---|---|---|---|---|---|---|---|---|---|
| 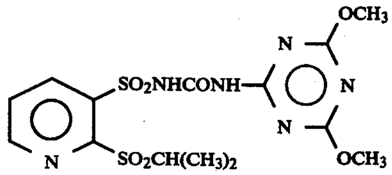 Compound 19 | .05 | 3C, 9H | 3C, 9G | 0 | 2C, 9G | 2C, 9H | 10E | 3H | 1C | 3H, 2C | 3H | 0 | 5G | 7G |
| 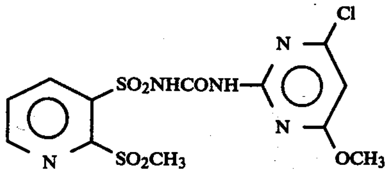 Compound 20 | .5 | 10H | 9G | 3C, 7H | 3C, 8G | 3C, 8G | 10E | 4C, 9H | 2C | 9G | 9H | 3C, 9G | 10E | 4C, 9G |
| 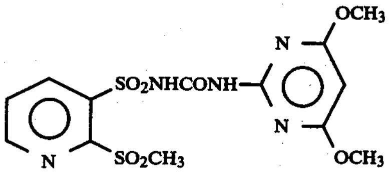 Compound 21 | .5 | 10E | 10E | 9H | 6C, 9H | 6C, 9H | 10E | 6C, 9H | 6C, 9G | 9G | 9H | 9G | 10E | — |
| 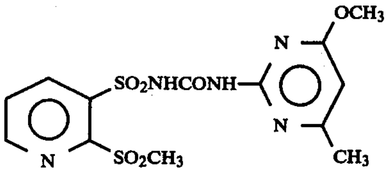 Compound 22 | .5 | 10E | 10E | 9H | 10E | 6C, 9H | 10E | 6C, 9H | 6C, 9G | 9C | 9H | 2C, 9G | 10E | — |
| 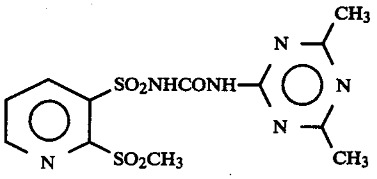 Compound 23 | .5 | 2C, 8G | 2C, 5G | 0 | 5G | 0 | 2C, 5G | 2C | 0 | 1C | — | 1C | 3G | — |

TABLE A-continued
| | | | | | | | | | | | | | | |
|---|---|---|---|---|---|---|---|---|---|---|---|---|---|---|
| 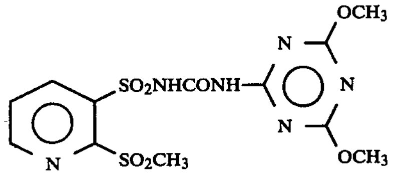 | .5 | 10H | 2C, 9H | 2G | 2C, 9G | 3C, 9H | 10E | 3C, 9H | 5G | 9G | 9H | 9G | 7G | — |
| Compound 24 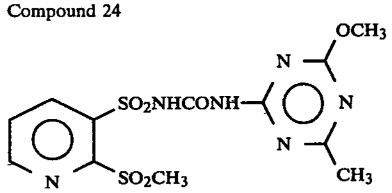 | .5 | 6C, 9H | 9H | 4H | 2C, 9G | 2C, 9G | 10E | 2C, 9H | 2C, 5G | 2C, 8G | 8H | 9G | 3G | — |
| Compound 25 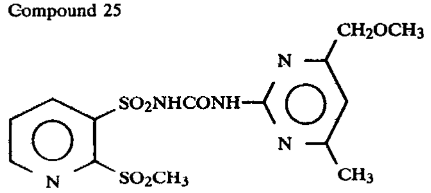 | .05 | 2C, 9G | 3C, 7G | 0 | 2C, 8G | 2C, 5G | 4C, 9H | 3C, 7G | 3C | 0 | 8H | 0 | 1C, 6G | — |
| Compound 26 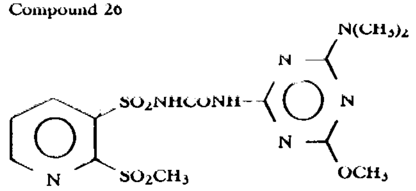 | .05 | 5C, 9H | 2C, 8G | 1C, 1H | 8H | 3C, 7G | 10E | 2C, 3G | 1C, 6G | 5G | | 9G | 10E | — |

Test B

Two plastic bulb pans were filled with fertilized and limed Woodstown sandy loam. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatus*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated preemergence with several test compounds within the scope of the invention.

Twenty-eight days after treatment, the plants were evaluated and visually rated for response to the chemical treatments utilizing the rating system described previously for Test A. The data are summarized in Table B. Note that the compounds are highly active herbicides.

TABLE B

PRE-EMERGENCE ON WOODSTOWN SANDY LOAM

| | Compound 2 | | Compound 20 | | | | Compound 21 | | | | Compound 6 | | Compound 25 | |
|---|---|---|---|---|---|---|---|---|---|---|---|---|---|---|
| Rate kg/ha | .015 | .060 | .007 | .015 | .030 | .120 | .007 | .015 | .030 | .120 | .030 | .120 | .030 | .120 |
| Crabgrass | 5G | 8G | 8G, 8C | 9G, 9C | 10C | 10C | 5G | 7G, 3H | 10C | 10C | 0 | 0 | 6G | 8G |
| Barnyard-grass | 7G, 3H | 8G, 5C | 8G, 5H | 8G, 5H | 9G, 9C | 10C | 6G | 7G | 7G, 8C | 10C | 0 | 2G | 3G | 2H, 5G |
| Sorghum | 10C | 10C | 10C | 10C | 10C | 10E | 10C | 10C | 10E | 10C | 7G, 5H | 8G, 6C | 2G | 9G, 9C |
| Wild Oats | 7G, 3C | 7G, 3C | 7G | 8G, 3C | 7G, 9C | 10C | 6G | 6G | 6G, 4C | 7G, 8C | 2G | 6G, 5H | 0 | 2G |
| Johnsongrass | 8G, 3H | 8G, 5H | 9G, 9C | 9G, 9C | 10C | 10C | 8G, 3H | 9G, 9C | 8G, 5H | 10C | 2G, 5H | 7G, 5H | 8G | 9G |
| Dallisgrass | 0 | 5G | 8G | 8G, 3H | 8G, 3H | 9G, 9C | 2G | 4G | 6G | 9G, 9C | 0 | 0 | 0 | 4G |
| Giant foxtail | 6G, 3H | 9G, 9C | 8G, 5H | 10C | 10C | 10C | 6G | 10C | 10C | 10C | 0 | 0 | 0 | 0 |
| Ky. bluegrass | 7G | 9G, 9C | 7G, 5C | 8G, 9C | 10C | 10C | 5G | 7G, 5C | 10C | 10C | — | — | 0 | 5G |
| Cheatgrass | 9G | 9G | 10C | 10C | 10C | 10C | 10E | 10E | 10E | 10E | 0 | 5G | 0 | 3G |
| Sugarbeets | 8G | 9G | 7G, 8C | 10C | 10C | 10C | 6G, 5C | 8G, 8C | 9G, 9C | 10C | 3G | 7G | 0 | 5G |
| Corn | 8G, 7H | 9G, 9C | 6G, 5H | 8G, 5H | 9G, 9C | 10C | 4G | 7G, 5H | 8G, 5C | 9G, 8C | 0 | 9G, 9C | 0 | 3G |
| Mustard | 9G | 9G | 9G, 8C | 9G, 8C | 10C | 10C | 9G, 6C | 10C | 10C | 10C | 0 | 0 | 0 | 2G |
| Cocklebur | 6G | 6G | 8G, 3H | 8G, 5H | 8G, 5H | 9G, 8C | 5G | 6G | 7G, 3H | 8G, 3H | 0 | 5G | 0 | 2G |
| Pigweed | — | — | 8G, 9C | 10E | 10C | 10E | 8G, 8C | 8G, 8C | 10E | 9G, 9C | — | — | — | — |
| Nutsedge | 10C | 10C | 8G | 10E | 9G | 10E | 4G | 8G | 8G | 10E | 2G | 4G | 4G | 4G |
| Cotton | 3G | 6G | 5G | 9G | 8G, 3H | 9G, 9C | 2G | 5G, 5H | 8G, 5H | 9G, 5C | 0 | 5G, 3H | 0 | 0 |
| Morningglory | 3G | 5G | 5G | 6G, 5H | 7G | 9G, 3C | 4G | 8G, 5H | 6G | 9G, 5C | 0 | 4G | 0 | 0 |
| Sicklepod | 10C | 8G | 4G | 8G | 9G, 3C | 9G, 7C | 4G | 5G | 7G | 9G, 5C | 0 | 2G | 0 | 0 |
| Teaweed | — | — | 3G | 7G, 3H | 8G, 5C | 9G, 9C | 0 | 2G | 5G | 8G, 5C | 0 | 0 | 2G | 2G |
| Velvetleaf | 8G | 9G | 5G, 5H | 8G, 5H | 9G, 9C | 10C | 3G | 6G, 5H | 8G, 5H | 10C | 0 | 0 | — | 9G |
| Jimsonweed | 8G, 8C | 9G, 9C | 8G, 3C | 10C | 10C | 9G, 9C | 6G | 8G, 3H | 8G, 5C | 9G, 9C | 0 | 0 | 0 | 2G |
| Soybean | 5G | 8G | 0 | 6G, 5H | 6G | 9G, 8C | 0 | 5G, 5H | 6G, 5H | 8G, 5H | 0 | 5G | 0 | 2G |
| Rice | 10C | 10C | 10E | 10E | 10C | 10E | 10E | 10E | 10E | 10E | 10C | 10C | 6G | 10C |
| Wheat | 6G | 7G | 6G | 8G, 7C | 6G, 3C | 7G, 8C | 7G | 8G, 7C | 6G, 3C | 10C | 0 | 0 | 0 | 2G |

What is claimed is:

1. A compound of the formula:

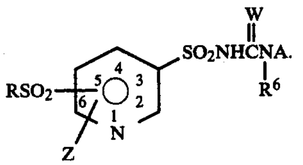

wherein

R is $C_1$–$C_6$ alkyl, $C_3$–$C_6$ alkenyl, $C_2$–$C_4$ alkoxyalkyl, $C_5$–$C_6$ cycloalkyl, $R^1OCH_2CH_2OCH_2$, $R^1OCH_2CH_2OCH_2CH_2$,

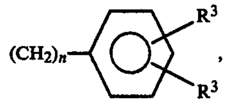

$CF_3$, $CF_3CH_2$ or HGLCCF$_2$, $HCF_2$ $R^1$ is methyl or ethyl;

$R^2$ and $R_3$ are independently H, Cl, $OCH_3$, F, $CH_3$, Br, $NO_2$ or $CF_3$;

n is 0, 1 or 2;

G is F, Cl, Br or $CF_3$;

L is F, Cl or H;

Z is H, F, Cl, Br, $CH_3$, $CH_3O$ or $CH_3S$;

W is O or S:

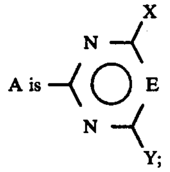

X is $CH_3$, $CH_3O$ or Cl;

Y is $CH_3$, $CH_3CH_2$, $CH_3O$, $CH_3CH_2O$, $CH_3O(CH_2)_m$, $CH_3OCH_2CH_2O$, $R^4O_2CR^5CHO$, $(CH_3)_2N$, $CH_3(CH_2CN)N$, $NHCH_3$ or $NH_2$;

E is N;

$R^4$ is H, $CH_3$ or $CH_3CH_2$;

$R^5$ is H or $CH_3$;

$R^6$ is H or $CH_3$;

m is 1 or 2;

and their agriculturally suitable salts; provided that:

(1) when W=S, then $R^6$ is H; and (2) when X=Cl, then E=CH and Y=$CH_3$, $C_2H_5$, $CH_3O$, $C_2H_5O$, $CH_3O(CH_2)_m$—, $NH_2$, $NHCH_3$ or $N(CH_3)_2$.

2. Compounds of claim 1 where

R is $C_1$–$C_6$ alkyl, $C_3$–$C_6$ alkenyl, $C_2$–$C_4$ alkoxyalkyl, $C_5$–$C_6$ cycloalkyl, $R^1OCH_2CH_2OCH_2$, $R^1OCH_2CH_2OCH_2CH_2$,

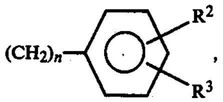

$CF_3$, $CF_3CH_2$ or HGLCCF$_2$;

$R^1$ is methyl or ethyl;

$R^2$ and $R^3$ are independently H, Cl, $OCH_3$, F, $CH_3$, Br, $NO_2$ or $CF_3$;

n is 0, 1 or 2;

G is F, Cl, Br or $CF_3$;

L is F, Cl or H;

Z is H, F, Cl, Br, $CH_3$, $CH_3O$ or $CH_3S$;

W is O or S;

A is 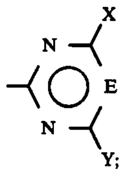

X is $CH_3$ or $CH_3O$;

Y is $CH_3$, $CH_3CH_2$, $CH_3O$, $CH_3CH_2O$, $CF_3CH_2O$, $CH_3O(CH_2)_m$, $CH_3OCH_2CH_2O$, $R^4O_2CR^5CHO$, $(CH_3)_2N$ or $CH_3(CH_2CN)N$;

E is N;

$R^4$ is H, $CH_3$ or $CH_3CH_2$;

$R^5$ is H or $CH_3$;

$R^6$ is H;

m is 1 or 2;

and their agriculturally suitable salts.

3. Compounds of claim 1 or claim 2 wherein the substituent $RSO_2$ is at the 2-position of the pyridine ring.

4. Compounds of claim 3 wherein W is O.

5. Compounds of claim 4 wherein Z is H.

6. Compounds of claim 5 wherein R is $C_1$–$C_4$ alkyl.

7. Compounds of claim 6 wherein Y is $CH_3$, $CH_3O$ or $CH_3CH_2O$.

8. The compound of claim 1, N-[(4,6-dimethoxy-1,3,5-triazin-2-yl)aminocarbonyl]-2-(methylsulfonyl)-3-pyridinesulfonamide.

9. The compound of claim 1, N-[(4,6-dimethyl-1,3,5-triazin-2-yl)aminocarbonyl]-2-(methylsulfonyl)-3-pyridinesulfonamide.

10. The compound of claim 1, N-[(4-methoxy-6-methyl-1,3,5-triazin-2-yl)aminocarbonyl]-2-(methylsulfonyl)-3-pyridinesulfonamide.

11. The compound of claim 1, N-[(4-dimethylamino-6-methoxy-1,3,5-triazin-2-yl)aminocarbonyl]-2-(methylsulfonyl)-3-pyridinesulfonamide.

12. A composition suitable for controlling the growth of undesired vegetation which comprises an effective amount of a compound of claim 1 and at least one of the following: surfactant, solid or liquid diluent.

13. A composition suitable for controlling the growth of undesired vegetation which comprises an effective amount of a compound of claim 2 and at least one of the following: surfactant, solid or liquid diluent.

14. A composition suitable for controlling the growth of undesired vegetation which comprises an effective amount of a compound of claim 3 and at least one of the following: surfactant, solid or liquid diluent.

15. A composition suitable for controlling the growth of undesired vegetation which comprises an effective amount of a compound of claim 4 and at least one of the following: surfactant, solid or liquid diluent.

16. A composition suitable for controlling the growth of undesired vegetation which comprises an effective amount of a compound of claim 5 and at least one of the following: surfactant, solid or liquid diluent.

17. A composition suitable for controlling the growth of undesired vegetation which comprises an effective amount of a compound of claim 6 and at least one of the following: surfactant, solid or liquid diluent.

18. A method for controlling the growth of undesired vegetation which comprises applying to the locus to be protected an effective amount of a compound of claim 1.

19. A method for controlling the growth of undesired vegetation which comprises applying to the locus to be protected an effective amount of a compound of claim 2.

20. A method for controlling the growth of undesired vegetation which comprises applying to the locus to be protected an effective amount of a compound of claim 3.

21. A method for controlling the growth of undesired vegetation which comprises applying to the locus to be protected an effective amount of a compound of claim 4.

22. A method for controlling the growth of undesired vegetation which comprises applying to the locus to be protected an effective amount of a compound of claim 5.

23. A method for controlling the growth of undesired vegetation which comprises applying to the locus to be protected an effective amount of a compound of claim 6.

* * * * *